United States Patent
Malik

(10) Patent No.: US 11,986,474 B1
(45) Date of Patent: May 21, 2024

(54) METHODS FOR TREATING HEART FAILURE BY ADMINISTERING CARDIAC SARCOMERE ACTIVATORS

(71) Applicant: Cytokinetics, Incorporated, South San Francisco, CA (US)

(72) Inventor: Fady Malik, Burlingame, CA (US)

(73) Assignee: CYTOKINETICS, INCORPORATED, South San Francisco, CA (US)

(*) Notice: Subject to any disclaimer, the term of this patent is extended or adjusted under 35 U.S.C. 154(b) by 0 days.

(21) Appl. No.: 18/342,387

(22) Filed: Jun. 27, 2023

(51) Int. Cl.
*A61K 31/496* (2006.01)
*A61P 9/04* (2006.01)

(52) U.S. Cl.
CPC .............. *A61K 31/496* (2013.01); *A61P 9/04* (2018.01)

(58) Field of Classification Search
CPC ................................ A61K 31/496; A61P 9/04
See application file for complete search history.

(56) References Cited

U.S. PATENT DOCUMENTS

| | | | |
|---|---|---|---|
| 4,450,150 A | 5/1984 | Sidman | |
| 6,303,144 B1 | 10/2001 | Omura | |
| 7,507,735 B2 | 3/2009 | Morgan et al. | |
| 8,101,617 B2 | 1/2012 | Morgan et al. | |
| 8,110,595 B2 | 2/2012 | Morgan et al. | |
| 8,445,495 B2 | 5/2013 | Morgan et al. | |
| 8,513,257 B2 | 8/2013 | Morgan et al. | |
| 8,871,768 B2 | 10/2014 | Morgan et al. | |
| 8,871,769 B2 | 10/2014 | Morgan et al. | |
| 9,150,564 B2 | 10/2015 | Morgan et al. | |
| 9,643,925 B2 | 5/2017 | Morgan et al. | |
| 9,895,308 B2 | 2/2018 | Caldwell | |
| 9,951,015 B2 | 4/2018 | Bi et al. | |
| 9,988,354 B2 | 6/2018 | Cui et al. | |
| 10,035,770 B2 | 7/2018 | Morgan et al. | |
| 10,385,023 B2 | 8/2019 | Morgan et al. | |
| 10,421,726 B2 | 9/2019 | Bi et al. | |
| 10,543,215 B2 | 1/2020 | Scott et al. | |
| 10,975,034 B2 | 4/2021 | Morgan et al. | |
| 11,040,956 B2 | 6/2021 | Caille et al. | |
| 11,384,053 B2 | 7/2022 | Bi et al. | |
| 11,465,969 B2 | 10/2022 | Morrison et al. | |
| 11,472,773 B2 | 10/2022 | Cui et al. | |
| 11,576,910 B2 | 2/2023 | Honarpour et al. | |
| 2006/0014761 A1 | 1/2006 | Morgan et al. | |
| 2007/0161617 A1 | 7/2007 | Morgan et al. | |
| 2009/0036447 A1 | 2/2009 | Morgan et al. | |
| 2009/0099198 A1 | 4/2009 | Morgan et al. | |
| 2010/0029680 A1 | 2/2010 | Morgan et al. | |
| 2012/0172372 A1 | 7/2012 | Morgan et al. | |
| 2013/0324549 A1 | 12/2013 | Morgan et al. | |
| 2014/0038983 A1 | 2/2014 | Morgan et al. | |
| 2014/0309235 A1 | 10/2014 | Bi et al. | |
| 2015/0005296 A1 | 1/2015 | Morgan et al. | |
| 2016/0015628 A1 | 1/2016 | Caldwell | |
| 2016/0016906 A1 | 1/2016 | Cui et al. | |
| 2016/0115133 A1 | 4/2016 | Morgan et al. | |
| 2017/0267638 A1 | 9/2017 | Morgan et al. | |
| 2018/0140611 A1 | 5/2018 | Scott et al. | |
| 2018/0273479 A1 | 9/2018 | Bi et al. | |
| 2018/0305316 A1 | 10/2018 | Morgan et al. | |
| 2018/0312469 A1 | 11/2018 | Cui et al. | |
| 2019/0352267 A1 | 11/2019 | Morgan et al. | |
| 2020/0079736 A1 | 3/2020 | Cui et al. | |
| 2020/0108076 A1 | 4/2020 | Scott et al. | |
| 2020/0155547 A1 | 5/2020 | Honarpour et al. | |
| 2020/0277261 A1 | 9/2020 | Bi et al. | |
| 2020/0308143 A1 | 10/2020 | Caille et al. | |
| 2020/0331859 A1 | 10/2020 | Cui et al. | |
| 2020/0399221 A1 | 12/2020 | Cui et al. | |
| 2021/0198203 A1 | 7/2021 | Morgan et al. | |
| 2021/0221772 A1 | 7/2021 | Man et al. | |
| 2021/0292271 A1 | 9/2021 | Brasola et al. | |
| 2021/0371397 A1 | 12/2021 | Caille et al. | |

(Continued)

FOREIGN PATENT DOCUMENTS

| | | |
|---|---|---|
| WO | 9940942 A1 | 8/1999 |
| WO | 0032218 A1 | 6/2000 |

(Continued)

OTHER PUBLICATIONS

Adjei, A. et al. (Jun. 7, 1990). "Pulmonary Delivery of Peptide Drugs: Effect of Particle Size on Bioavailability of Leuprolide Acetate in Healthy Male Volunteers," Pharm Res. 7(6):565-569.

Ambrosy, A. P. et al. (Apr. 1, 2014, e-pub. Feb. 5, 2014). "The Global Health and Economic Burden of Hospitalizations for Heart Failure: Lessons Learned From Hospitalized Heart Failure Registries," J Am Coll Cardiol. 63(12):1123-1133.

Anonymous (Apr. 4, 2016). "Cytokinetics Announces Start of Phase 2 Clinical Trial of Omecamtiv Mecarbil in Japanese Subjects With Heart Failure," Globe Newswire, 5 pages.

Anonymous (Dec. 1, 2016). "Cytokinetics Announces Start of GALACTIC-HF, A Phase 3 Clinical Trial of Omecamtiv Mecarbil," Globe Newswire, 6 pages.

(Continued)

*Primary Examiner* — Sarah Pihonak
(74) *Attorney, Agent, or Firm* — MORRISON & FOERSTER LLP

(57) ABSTRACT

Methods for treating heart failure are described herein. Treatment methods include administering a cardiac sarcomere activator (e.g., omecamtiv mecarbil, or a pharmaceutically acceptable salt and/or hydrate thereof) to a subject in need thereof. Treatment methods also include adjusting a dose level of the CSA, for example, to increase, decrease, or maintain a dose level, based on the subject's plasma concentration of the CSA determined after administration of the first dose level of the CSA has started. Provided herein are also treatment methods effective to achieve a target concentration range of the CSA and dose in a single step following a single plasma concentration determination.

30 Claims, 2 Drawing Sheets

(56) References Cited

U.S. PATENT DOCUMENTS

| | | |
|---|---|---|
| 2022/0042055 A1 | 2/2022 | Bisagni et al. |
| 2022/0153700 A1 | 5/2022 | Cui et al. |
| 2022/0184068 A1 | 6/2022 | Honarpour et al. |
| 2022/0185779 A1 | 6/2022 | Morgan et al. |
| 2022/0298099 A1 | 9/2022 | Caille et al. |
| 2022/0298114 A1 | 9/2022 | Bi et al. |
| 2023/0044617 A1 | 2/2023 | Cui et al. |
| 2023/0090391 A1 | 3/2023 | Bi et al. |
| 2023/0108971 A1 | 4/2023 | Morrison et al. |
| 2023/0149394 A1 | 5/2023 | Honarpour et al. |
| 2023/0355615 A1 | 11/2023 | Honarpour et al. |
| 2023/0373955 A1 | 11/2023 | Caille et al. |

FOREIGN PATENT DOCUMENTS

| | | | |
|---|---|---|---|
| WO | 2004033036 A2 | 4/2004 | |
| WO | 2007133747 A2 | 11/2007 | |
| WO | 2007141411 A1 | 12/2007 | |
| WO | 2008130158 A1 | 10/2008 | |
| WO | 2014152236 A1 | 9/2014 | |
| WO | 2016210240 A1 | 12/2016 | |
| WO | 2019006235 A1 | 1/2019 | |
| WO | 2020011626 A1 | 1/2020 | |
| WO | 2020014406 A1 | 1/2020 | |
| WO | 2021053175 A1 | 3/2021 | |
| WO | 2021053189 A1 | 3/2021 | |
| WO | 2021070123 A1 | 4/2021 | |
| WO | 2021070124 A1 | 4/2021 | |
| WO | 2021136477 A1 | 7/2021 | |
| WO | WO-2022103966 A1 * | 5/2022 | ........... A61K 31/496 |
| WO | 2023205291 A2 | 10/2023 | |

OTHER PUBLICATIONS

Anonymous (Mar. 13, 2015). "Cytokinetics Announces Completion of Enrollment in Cosmic-HF," Cytokinetics, Inc., 7 pages.

Anonymous (May 1, 2017). "Cytokinetics Announces Results From Dose Escalation Phase of Cosmic-HF Presented at Heart Failure 2017," Globe Newswire, 6 pages.

Anonymous (Nov. 30, 2016). "The Lancet Publishes Results From Cosmic-HF Trial Showing Omecamtiv Mecarbil Significantly Improved Cardiac Function in Patients With Chronic Heart Failure," Globe Newswire, 13 pages.

Anonymous (Oct. 27, 2015). "Amgen and Cytokinetics Announce Positive Top-Line Results From Cosmic-HF, A Phase 2 Trial of Omecamtiv Mecarbil in Patients With Chronic Heart Failure," Globe Newswire, 11 pages.

Anonymous (Sep. 1, 2016). "Cytokinetics and Amgen to Advance Omecamtiv Mecarbil to Phase 3 Clinical Development," Globe Newswire, 6 pages.

Anonymous. (Last Reviewed Jun. 7, 2023). "Classes and Stages of Heart Failure," American Heart Association, Retrieved from Internet: https://www.heart.org/en/health-topics/heart-failure/what-is-heart-failure/classes-of-heart-failure, 3 pages.

Apple, F. S. et al. (Jul. 2009, e-pub. May 28, 2009). "A New Season for Cardiac Troponin Assays: It's Time to Keep a Scorecard," Clin Chem. 55(7): 1303-1306.

Berge, S. et al. (Jan. 1977). "Pharmaceutical Salts," Journal of Pharmaceutical Sciences 66(1):1-19.

Bhatia, R. S. et al. (Jul. 20, 2006). "Outcome of Heart Failure With Preserved Ejection Fraction in a Population-Based Study," N Engl J Med. 355(3):260-269.

Biering-Sorensen, T. et al. (Aug. 2015). "Systolic Ejection Time is an Independent Predictor of Incident Heart Failure in a Community Based Cohort Free of Heart Failure," Journal of Cardiac Failure 21(8 Supplement):S84, 1 page.

Braunwald, E. et al. (Nov. 9, 1967). "Mechanisms of Contraction of the Normal and Failing Heart," N Engl J Med 277(19):1012-1022.

Bretz, F. et al. (Feb. 15, 2009, e-pub. Dec. 2, 2008). "A Graphical Approach to Sequentially Rejective Multiple Test Procedures," Stat Med. 28(4):586-604.

Chen, P-W. et al. (Apr. 1, 2022). "Population Pharmacokinetic Properties of Omecamtiv Mecarbil in Healthy Subjects and Patients With Heart Failure With Reduced Ejection Fraction," J Cardiovasc Pharmacol. 79(4):539-548.

Cleland, J. et al. (Aug. 5, 2008). "Predicting the Long-Term Effects of Cardiac Resynchronization Therapy on Mortality From Baseline Variables and the Early Response a Report From the CARE-HF (Cardiac Resynchronization in Heart Failure) Trial," J Am Coll Cardiol. 52(6):438-445.

Cleland, J. G. F. et al. (Nov. 10, 2009). "Plasma Concentration of Amino-Terminal Pro-Brain Natriuretic Peptide in Chronic Heart Failure: Prediction Of Cardiovascular Events and Interaction With the Effects of Rosuvastatin: A Report From CORONA (Controlled Rosuvastatin Multinational Trial in Heart Failure)," J Am Coll Cardiol. 54(20):1850-1859.

Cleland, J.G.F. et al. (Aug. 20, 2011). "The Effects of the Cardiac Myosin Activator, Omecamtivmecarbil, On Cardiac Function in Systolic Heart Failure: A Double-Blind, Placebo Controlled, Crossover, Dose-Ranging Phase 2 Trial," Lancet 378:676-683.

clincialtrials.gov (Jun. 21, 2017). "History of Changes for Study: NCT02929329: Registrational Study With Omecamtiv Mecarbil/AMG 423 to Treat Chronic Heart Failure With Reduced Ejection Fraction (GALACTIC-HF)," 30 pages.

clincialtrials.gov (May 15, 2017). History of Changes for Study: NCT02695420: Safety, PK, and Efficacy of Omecamtiv Mercarbil in Japanese Subjects with Heart Failure With Reduced Ejection Fraction ClinicalTrials.gov, retrieved from the Internet https://clinicaltrials.gov/ct2/history/NCT02695420?A=15&B=15&C=merged#StudyPageTop, last visited Jun. 22, 2022, 7 pages.

clincialtrials.gov (May 15, 2017). "History of Changes for Study: NCT02695420: Safety, PK, and Efficacy of Omecamtiv Mercarbil in Japanese Subjects with Heart Failure With Reduced Ejection Fraction," 6 pages.

clinicaltrials.gov (May 5, 2016; downloaded from the web Nov. 19, 2021). "NCT01786512—COSMIC-HF—Chronic Oral Study of Myosin Activation to Increase Contractility in Heart Failure," 10 pages.

Cytokinetics. (2022). "Empowering Muscle Empowering Lives. Sarcomere Directed Therapies," Cytokinetics 2022, 58 pages.

Dasgupta, A. et al. (2008). "Analytical Techniques for Measuring Concentrations of Therapeutic Drugs in Biological Fluids," Chapter 3 in Handbook of Drug Monitoring Methods, Humana Press, pp. 67-86.

Deluca, P. P. et al. (1982). "Parenteral Drug-Delivery Systems," Chapter 8 in Pharmaceutics and Pharmacy Practice, J. B. Lippincott Company, pp. 238-250, 16 pages.

Dickstein, K. et al. (Oct. 2008, e-pub. Sep. 17, 2008). "ESC Guidelines for the Diagnosis and Treatment of Acute and Chronic Heart Failure 2008: The Task Force for the Diagnosis and Treatment of Acute and Chronic Heart Failure 2008 of the European Society of Cardiology. Developed in Collaboration With the Heart Failure Association of the ESC (HFA) and Endorsed by the European Society of Intensive Care Medicine (ESICM)," Eur Heart J. 29(19):2388-2442, 55 pages.

Go, A. S. et al. (Jan. 1, 2013, e-pub. Dec. 12, 2012). "Heart Disease and Stroke Statistics—2013 Update: A Report From the American Heart Association," Circulation 127(1):e6-e245, 489 pages.

Greenberg, B. H. et al. (Jan. 2015, e-pub. Nov. 11, 2014). "Safety and Tolerability of Omecamtiv Mecarbil During Exercise in Patients With Ischemic Cardiomyopathy and Angina," JACC Heart Fail. 3(1):22-29.

Greene, S. J. et al. (Apr. 2015, e-pub. Feb. 10, 2015). "The Vulnerable Phase After Hospitalization for Heart Failure," Nat Rev Cardiol. 12(4):220-229.

Hampton, J. R. et al. (Apr. 5, 1997). "Randomised Study of Effect of Ibopamine on Survival in Patients With Advanced Severe Heart Failure. Second Prospective Randomised Study of Ibopamine on Mortality and Efficacy (PRIME II) Investigators," Lancet. 349(9057):971-977.

Hasenfuss, G. et al. (Aug. 2011, e-pub. Mar. 8, 2011). "Cardiac Inotropes: Current Agents and Future Directions," Eur Heart J. 32(15):1838-1845.

(56) References Cited

OTHER PUBLICATIONS

Haybittle, J.L. (Oct. 1971). "Repeated Assessment of Results in Clinical Trials of Cancer Treatment," Br J Radiol 44(526):793-797.

Hicks, K. A. et al. (Jul. 28, 2015, e-pub. Dec. 29, 2014). "2014 ACC/AHA Key Data Elements and Definitions for Cardiovascular Endpoint Events in Clinical Trials: A Report of the American College of Cardiology/American Heart Association Task Force on Clinical Data Standards (Writing Committee to Develop Cardiovascular Endpoints Data Standards)," J Am Coll Cardiol. 66(4):403-469.

Hicks, K.A. et al. (Mar. 6, 2018). "2017 Cardiovascular and Stroke Endpoint Definitions for Clinical Trials," J Am Coll Cardiol 71(9):1021-1034.

Hilfiker-Kleiner, D. et al. (Nov. 7, 2006). "Molecular Mechanisms in Heart Failure: Focus on Cardiac Hypertrophy, Inflammation, Angiogenesis, and Apoptosis," J Am Coll Cardiol. 48(9 Suppl. A):A56-A66.

International Preliminary Report on Patentability, dated Dec. 31, 2019, for PCT Application No. PCT/US2018/040181, filed on Jun. 29, 2018, 7 pages.

International Search Report and Written Opinion of the International Searching Authority, dated Sep. 27, 2018, for PCT Application No. PCT/US2018/040181, filed on Jun. 29, 2018, 10 pages.

Jencks, S. F. et al. (Apr. 2, 2009). "Rehospitalizations Among Patients in the Medicare Fee-for-Service Program," N Engl J Med. 360(14):1418-1428.

Jessup, M. et al. (May 15, 2003). "Heart Failure," N Engl J Med. 348(20):2007-2018.

Kang, J. S. et al. (Mar. 2009). "Overview of Therapeutic Drug Monitoring," Korean J Intern Med. 24(1):1-10.

Kannankeril, P.J. et al. (Nov. 15, 2002). "Usefulness of Troponin I as a Marker of Myocardial Injury After Pediatric Cardiac Catheterization," Am J Cardiol. 90(10):1128-1132.

Kawashima, Y. et al. (Nov. 1, 1999). "Pulmonary Delivery of Insulin With Nebulized DL-Lactide/Glycolide Copolymer (PLGA) Nanospheres to Prolong Hypoglycemic Effect," J Control Release 62(1-2):279-287.

Klinkenberg, L. J. J. et al. (May 6, 2014, e-pub. Feb. 26, 2014). "Circulating Cardiac Troponin T Exhibits a Diurnal Rhythm," J Am Coll Cardiol. 63(17):1788-1795.

Kramer, D.G. et al. (Jul. 27, 2010). "Quantitative Evaluation of Drug or Device Effects on Ventricular Remodeling as Predictors of Therapeutic Effects on Mortality in Patients With Heart Failure and Reduced Ejection Fraction: A Meta-Analytic Approach," J Am Coll Cardiol 56(5):392-406, 30 pages.

Krum, H. et al. (Aug. 20, 2011). "Medical Therapy for Chronic Heart Failure," Lancet. 378(9792):713-721.

Levy, W. C. et al. (Mar. 21, 2006, e-pub. Mar. 13, 2006). "The Seattle Heart Failure Model: Prediction of Survival in Heart Failure," 113(11):1424-1433.

Liu, F. Y. et al. (Feb. 1993). "Pulmonary Delivery of Free and Liposomal Insulin," Pharm Res. 10(2):228-232.

Liu, L. C. et al. (2016, e-pub. Dec. 19, 2015). "Omecamtiv Mecarbil: A New Cardiac Myosin Activator for the Treatment of Heart Failure," Expert Opinion on Investigational Drugs 25(1):117-127.

Lopez-Sendon, J. (Jan. 2011). "The Heart Failure Epidemic," Medicographia 33(4):363-369.

Malik, F.I. et al. (Mar. 18, 2011). "Cardiac Myosin Activation: A Potential Therapeutic Approach for Systolic Heart Failure," Science 331(6023):1439-1443, 15 pages.

Malik, F.I. et al. (Oct. 2011, e-pub. May 17, 2011). "Cardiac Myosin Activation Part 1: From Concept to Clinic," J Mol Cell Cardiol. 51(4):454-461.

McLlvennan, C. K. et al. (Dec. 2014, e-pub. Aug. 20, 2014). "Outcomes in Acute Heart Failure: 30-Day Readmission Versus Death," Curr Heart Fail Rep. 11(4):445-452.

Mozaffarian, D. et al. (Jul. 24, 2007, e-pub. Jul. 9, 2007). "Prediction of Mode of Death in Heart Failure: the Seattle Heart Failure Model," Circulation 116(4):392-398.

Nagy, L. et al. (Sep. 2014). "Inotropes and Inodilators for Acute Heart Failure: Sarcomere Active Drugs in Focus," J Cardiovasc Pharmacol. 64(3):199-208.

Packer, M. (Jul. 15, 1993). "The Search for the Ideal Positive Inotropic Agent," N Engl J Med. 329(3):201-202.

Packer, M. et al. (Nov. 21, 1991). "Effect of Oral Milrinone on Mortality in Severe Chronic Heart Failure. The PROMISE Study Research Group," N Engl J Med. 325(21):1468-1475.

Palaparthy, R. et al. (Mar. 1, 2016, e-pub. Dec. 28, 2015). "Relative Bioavailability, Food, Effect and Safety of the Single-Dose Pharmacokinetics of Omecamtiv Mecarbil Following Administration of Different Modified-Release Formulations in Healthy Subjects," International Journal of Clinical Pharmacology and Therapeutics 54(3):217-227.

Peto, R. et al. (Dec. 1976). "Design and Analysis of Randomized Clinical Trials Requiring Prolonged Observation of Each Patient. I. Introduction and Design," Br J Cancer 34(6):585-612.

Ponikowski, P. et al. (Aug. 2016, e-pub. May 20, 2016). "2016 ESC Guidelines for the Diagnosis and Treatment of Acute and Chronic Heart Failure: The Task Force for the Diagnosis and Treatment of Acute and Chronic Heart Failure of the European Society of Cardiology (ESC). Developed With the Special Contribution of the Heart Failure Association (HFA) of the ESC," Eur J Heart Fail. 18(8):891-975.

Qian, F. et al. (Jan. 21, 2009, e-pub. Nov. 5, 2008). "Pulmonary Delivery of a GLP-1 Receptor Agonist, BMS-686117," Int J Pharm 366(1-2):218-220.

Qian, F. et al. (Jun. 5, 2009, e-pub. Mar. 19, 2009). "Sustained Release Subcutaneous Delivery of BMS-686117, a GLP-1 Receptor Peptide Agonist, via a Zinc Adduct," Int J Pharm. 374(1-2):46-52.

Rahimi, K. et al. (Oct. 2014, e-pub. Sep. 3, 2014). "Risk Prediction in Patients With Heart Failure: A Systematic Review and Analysis," JACC Heart Fail 2(5):440-446.

Shave, R. et al. (Jul. 13, 2010). "Exercise-Induced Cardiac Troponin Elevation: Evidence, Mechanisms, and Implications," J Am Coll Cardiol. 56(3):169-176.

Shen, Y.T. et al. (Jul. 2010). "Improvement of Cardiac Function by a Cardiac Myosin Activator in Conscious Dogs With Systolic Heart Failure," Circ Heart Fail 3(4):522-527.

Shih, J. H. (Dec. 1995). "Sample Size Calculation for Complex Clinical Trials With Survival Endpoints," Control Clin Trials. 16(6):395-407.

Solomon, S. D. et al. (Oct. 12, 2004, e-pub. Oct. 4, 2004). "Effect of Candesartan on Cause-Specific Mortality in Heart Failure Patients: The Candesartan in Heart Failure Assessment of Reduction in Mortality and Morbidity (CHARM) Program," Circulation 110(15):2180-2183.

Solomon, S. D. et al. (Sep. 7, 2010, e-pub. Aug. 23, 2010). "Effect of Cardiac Resynchronization Therapy on Reverse Remodeling and Relation to Outcome: Multicenter Automatic Defibrillator Implantation Trial: Cardiac Resynchronization Therapy," Circulation 122(10):985-992.

Steijns, L. S. W. et al. (Jun. 2002). "Evaluation of Fluorescence Polarization Assays for Measuring Valproic Acid, Phenytoin, Carbamazepine and Phenobarbital in Serum," Ther Drug Monit. 24(3):432-435.

Tacon, C. L. et al. (Mar. 2012, e-pub. Dec. 8, 2011). "Dobutamine for Patients With Severe Heart Failure: A Systematic Review and Meta-Analysis of Randomised Controlled Trials," Intensive Care Med. 38(3):359-367.

Teerlink, J. R. et al. (Dec. 10, 2016, e-pub. Dec. 1, 2016). "Chronic Oral Study of Myosin Activation to Increase Contractility in Heart Failure (COSMIC-HF): A Phase 2, Pharmacokinetic, Randomised, Placebo-Controlled Trial," Lancet. 388(10062):2895-2903.

Teerlink, J.R. et al. (2016). "Online Appendix: Acute Treatment With Omecamtiv Mecarbil to Increase Contractility in Acute Heart Failure: the ATOMIC AHF Study," J. Am. Coll. Cardiol. 67:1444-1455, Appendix, 16 pages.

Teerlink, J.R. et al. (Aug. 20, 2011). "Dose-Dependent Augmentation of Cardiac Systolic Function With the Selective Cardiac Myosin Activator, Omecamtiv Mecarbil: A First-in-Man Study," Lancet 378(9792):667-675.

(56) References Cited

OTHER PUBLICATIONS

Teerlink, J.R. et al. (Jan. 14, 2021, e-pub. Nov. 13, 2020). "Cardiac Myosin Activation with Omecamtiv Mecarbil in Systolic Heart Failure," N Engl J Med. 384(2):105-116.

Teerlink, J.R. et al. (Mar. 29, 2016). "Acute Treatment With Omecamtiv Mecarbil to Increase Contractility in Acute Heart Failure: The ATOMIC-AHF Study," J Am Coll Cardiol 67(12):1444-1455.

Teerlink, J.R. et al. (May 2014). "Chronic Oral Study of Myosin Activation to Increase Contractility in Heart Failure (COSMIC-HF): Improved Contractility and Evolution of Ventricular Remodelling Through Time," European Society of Cardiology—Heart Failure, 1 pages.

Thygesen, K. et al. (Oct. 16, 2012, e-pub. Sep. 5, 2012). "Third Universal Definition of Myocardial Infarction," J Am Coll Cardiol 60(16):1581-1598.

Trissel, L. A. et al. (1986). "Intravenous Infusion Solutions," ASHP Handbook on Injectable Drugs, 4th ed., pp. 622-630.

U.S. Appl. No. 15/898,303, filed Feb. 16, 2018, by William Brett Caldwell et al.(the U.S. Patent Application is not submitted herewith pursuant to the waiver of 37 C.F.R. § 1.98(a)(2)(iii) issued by the Office on Sep. 21, 2004.).

U.S. Appl. No. 17/176,003, filed Feb. 15, 2021, by Sheng Cui et al.(the U.S. Patent Application is not submitted herewith pursuant to the waiver of 37 C.F.R. § 1.98(a)(2)(iii) issued by the Office on Sep. 21, 2004.).

U.S. Appl. No. 18/313,267, filed May 5, 2023, by Narimon Honarpour et al. (the U.S. Patent Application is not submitted herewith pursuant to the waiver of 37 C.F.R. § 1.98(a)(2)(iii) issued by the Office on Sep. 21, 2004.).

Vu, T. et al. (Nov. 2015, e-pub. Jul. 14, 2015). "Population Pharmacokinetic-Pharmacodynamic Modeling of Omecamtiv Mecarbil, A Cardiac Myosin Activator, In Healthy Volunteers and Patients With Stable Heart Failure," J Clin Pharmacol. 55(11):1236-1247.

Waldenstrom, A. et al. (Jan. 17, 2014). "Role of Exosomes in Myocardial Remodeling," Circ Res. 114(2):315-324.

Wang, G-F. et al. (Nov. 2008). "Measurement of Plasma Concentration and Bioavailability of Nolatrexed Dihydrochloride in Mice," J South Med Univ 28(11):1993-1995, with English Abstract.

Weissler, A. M. et al. (Feb. 1968). "Systolic Time Intervals in Heart Failure in Man," Circulation 37(2):149-159.

Yancy, C. W. et al. (Oct. 15, 2013, e-pub. Jun. 5, 2013). "2013 ACCF/AHA Guideline for the Management of Heart Failure: A Report of the American College of Cardiology Foundation/American Heart Association Task Force on Practice Guidelines," Circulation 128(16):e240-e327.

Yancy, C. W. et al. (Sep. 27, 2016, e-pub. May 20, 2016). "2016 ACC/AHA/HFSA Focused Update on New Pharmacological Therapy for Heart Failure: An Update of the 2013 ACCF/AHA Guideline for the Management of Heart Failure: A Report of the American College of Cardiology/American Heart Association Task Force on Clinical Practice Guidelines and the Heart Failure Society of America," Circulation 134(13):e282-e293.

* cited by examiner

METHODS FOR TREATING HEART FAILURE BY ADMINISTERING CARDIAC SARCOMERE ACTIVATORS

BACKGROUND

The cardiac sarcomere is the basic unit of muscle contraction in the heart. The cardiac sarcomere is a highly ordered cytoskeletal structure composed of cardiac muscle myosin, actin and a set of regulatory proteins. The discovery and development of small molecule cardiac muscle myosin activators would lead to promising treatments for acute and chronic heart failure. Cardiac muscle myosin is the cytoskeletal motor protein in the cardiac muscle cell. It is directly responsible for converting chemical energy into the mechanical force, resulting in cardiac muscle contraction.

Current positive inotropic agents, such as beta-adrenergic receptor agonists or inhibitors of phosphodiesterase activity, increase the concentration of intracellular calcium, thereby increasing cardiac sarcomere contractility. However, the increase in calcium levels increases the velocity of cardiac muscle contraction and shortens systolic ejection time, which has been linked to potentially life-threatening side effects. In contrast, cardiac muscle myosin activators work by a mechanism that directly stimulates the activity of the cardiac muscle myosin motor protein, without increasing the intracellular calcium concentration. They accelerate the rate-limiting step of the myosin enzymatic cycle and shift it in favor of the force-producing state. Rather than increasing the velocity of cardiac contraction, this mechanism instead lengthens the systolic ejection time, which results in increased cardiac muscle contractility and cardiac output in a potentially more oxygen-efficient manner.

Omecamtiv mecarbil is a first in class, small molecule cardiac myosin activator, which is a type of myotrope that acts directly on the muscle fiber. Omecamtiv mecarbil, augments cardiac contractility by selectively binding to cardiac myosin increasing the number of force generators (myosin heads) that can bind to the actin filament and undergo a powerstroke once the cardiac cycle starts. In early clinical studies using short-term intravenous administration, omecamtiv mecarbil improved cardiac performance. In patients with chronic heart failure with reduced ejection fraction, treatment with omecamtiv mecarbil for 20 weeks increased left ventricular systolic function, decreased left ventricular systolic and diastolic volumes suggestive of beneficial reverse cardiac remodeling, and reduced natriuretic peptide concentrations and heart rate. In a randomized, placebo-controlled phase 3 clinical trial involving patients with heart failure and a reduced ejection fraction receiving guideline-based pharmacologic and device therapy, those in the omecamtiv mecarbil group had a lower relative risk of a heart-failure event or death from cardiovascular causes than those in the placebo group. This effect was observed without evidence of an increase in the risk of myocardial ischemic events, ventricular arrhythmias, or death from cardiovascular causes or any cause. The lowering of the incidence of the primary outcome was observed across a broad range of both inpatients and outpatients, including those with moderate or severe heart-failure symptoms and a reduced ejection fraction, systolic blood pressure, and renal function.

Many therapies have been developed that improve cardiovascular outcomes in patients with heart failure with reduced ejection fraction (HFrEF). However, none of the currently available drugs directly improve the central defect of HFrEF, reduced systolic function. Moreover, severe impairment of systolic function is often associated with lower blood pressure and greater difficulty tolerating target doses of guideline-directed medical therapies. Myotropes represent a new class of drugs that improve myocardial function by directly augmenting cardiac sarcomere function. The cardiac myosin activator, omecamtiv mecarbil, is the first of this class and it increases systolic function by selectively facilitating the actin-myosin interaction, increasing contractile force without altering the cardiomyocyte calcium transient.

Despite significant improvements in prognosis with contemporary medical therapy, HF with reduced ejection fraction (HFrEF) remains a progressive clinical syndrome and many patients develop worsening over time despite optimal guideline-based treatment. Regardless of terminology, these patients have a high burden of symptoms, recurrent HF hospitalizations, high mortality, and account for a large proportion of the total costs of HF care. As HF progresses, many patients become progressively intolerant of neurohormonal blockade with beta-blockers or renin-angiotensin-aldosterone system (RAAS) modulators due to hypotension or renal dysfunction, limiting their options for medical therapy. Selected patients with advanced HF may be candidates for other therapies such as cardiac transplantation or mechanical cardiac support, but these therapies are costly, highly invasive, and have limited availability. Intravenous inotropic therapy can be used for palliation of symptoms in selected patients but may be associated with increased mortality. Thus, there is a clear unmet need for effective and safe chronic medical therapies for patients with more advanced stages of HF.

The identification of safe drugs that increase cardiac performance has been a goal of heart failure therapeutics for more than a century, yet those that have been developed have consistently increased the incidence of myocardial ischemia, ventricular arrhythmias, or death due to their mechanism increasing intracellular calcium transients. As a selective cardiac myosin activator, omecamtiv mecarbil has been shown to have no effect on these transients.

Despite prior developments in this area, there remains a need for additional therapeutics for treating heart failure in patients, in particular, there remains a need for optimized dosing regimen of omecamtiv mecarbil with respect to treatment safety and efficacy.

BRIEF SUMMARY

Figure 1:
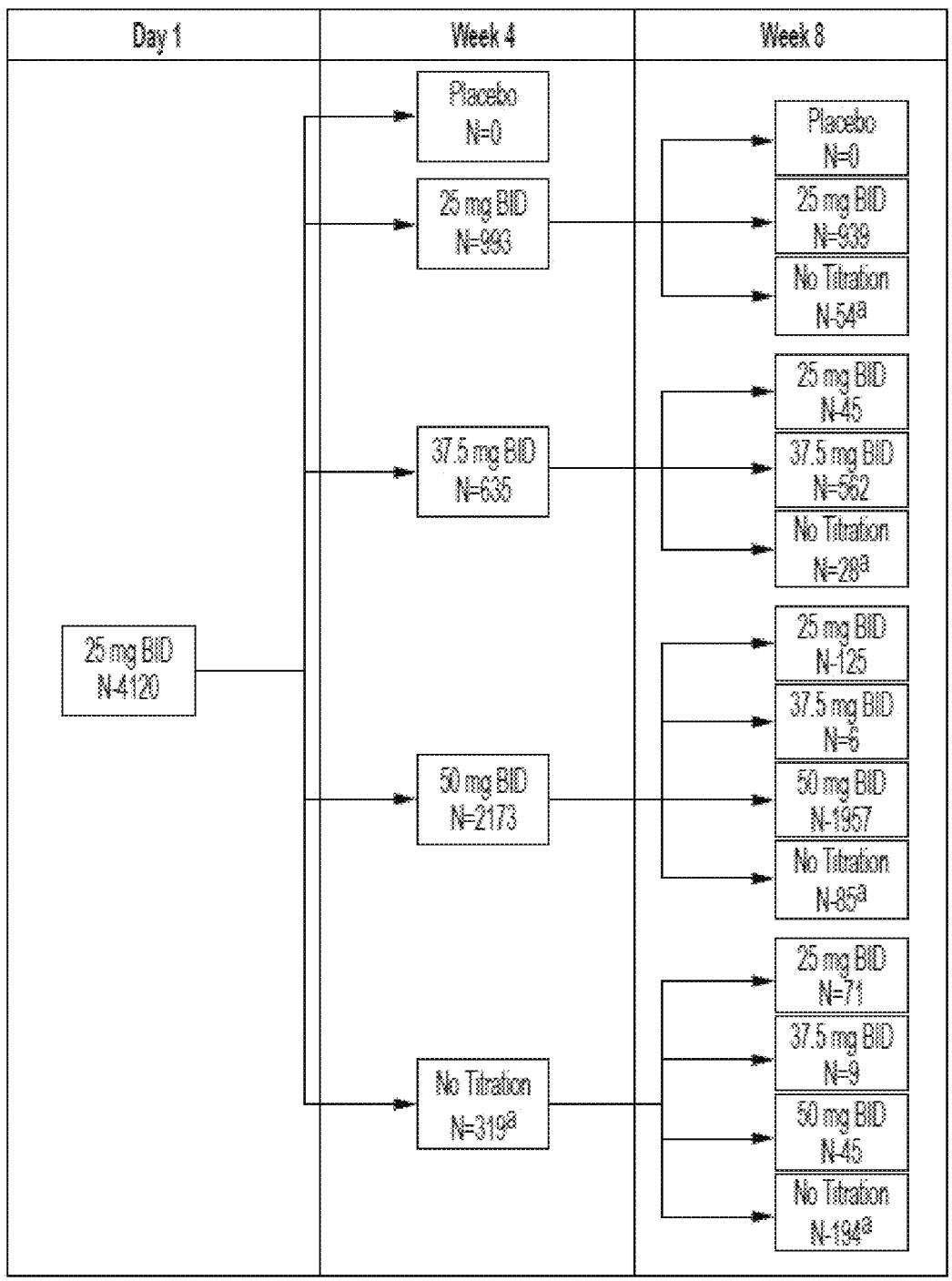
FIG. 1 shows an overview of dose changes during the titration phase of omecamtiv mecarbil.

Methods for treating heart failure are described herein. In some aspects, provided is a method of treating heart failure in a subject in need thereof, comprising: a) administering to the subject a first dose level of a cardiac sarcomere activator (CSA) of about 37.5 mg twice daily for an initial period of time; and b) administering to the subject a second dose level of the CSA for a second period of time based on the subject's plasma concentration of the CSA determined after administration of the first dose level of the CSA has started; wherein: b-i) when the subject's plasma concentration of the CSA is less than 300 ng/mL, the second dose level of the CSA is about 50 mg twice daily; b-ii) when the subject's plasma concentration of the CSA is greater than or equal to 300 ng/mL and less than or equal to 750 ng/ml, the second dose level of the CSA is about 37.5 mg twice daily; and b-iii) when the subject's plasma concentration of the CSA is greater than 750 ng/ml, the second dose level of the CSA is about 25 mg twice daily; and wherein the CSA is omecamtiv mecarbil, or a pharmaceutically acceptable salt thereof, or a hydrate of any of the foregoing.

Also provided is a method of treating heart failure in a subject in need thereof, comprising: a) administering to the subject a first dose level of a cardiac sarcomere activator (CSA) of about 37.5 mg twice daily for an initial period of time of at least about 2 weeks; and b) administering to the subject a second dose level of the CSA for a second period of time based on the subject's plasma concentration of the CSA, wherein the subject's plasma concentration of the CSA is determined at about 2-4 weeks after the first administration of the first dose level of the CSA, and the second dose level of the CSA is administered to the subject at about 4 weeks after the first administration of the first dose level of the CSA; wherein: b-i) when the subject's plasma concentration of the CSA is less than 300 ng/mL, the second dose level of the CSA is about 50 mg twice daily; b-ii) when the subject's plasma concentration of the CSA is greater than or equal to 300 ng/mL and less than or equal to 750 ng/ml, the second dose level of the CSA is about 37.5 mg twice daily; and b-iii) when the subject's plasma concentration of the CSA is greater than 750 ng/ml, the second dose level of the CSA is about 25 mg twice daily; and wherein the CSA is omecamtiv mecarbil, or a pharmaceutically acceptable salt thereof, or a hydrate of any of the foregoing, and wherein the treatment is effective to achieve a target plasma concentration of about 300 ng/mL to about 750 ng/mL during the second period of time.

DETAILED DESCRIPTION

Described herein are methods of treating heart failure using a cardiac sarcomere activator (CSA, e.g., omecamtiv mecarbil or a pharmaceutically acceptable salt thereof, or a hydrate of any of the foregoing). Treatment methods are effective to achieve a target concentration range of the CSA (e.g., about 300 ng/mL to about 750 ng/mL) and dose in a single step following a single plasma concentration determination. Treatment methods include administering to a subject in need thereof a first dose level of a CSA of at least about 30 mg twice daily (e.g., about 37.5 mg twice daily) for an initial period of time (e.g., at least about 2 weeks). Treatment methods also include adjusting a dose level of the CSA, for example, to increase, decrease, or maintain a dose level, based on the subject's plasma concentration of the CSA determined after administration of the first dose level of the CSA has started. For example, a dose level of the CSA may be increased, if the subject's plasma concentration of the CSA, determined after administration of the first dose level of the CSA has started, is less than a first threshold concentration (e.g., about 300 ng/mL). A dose level of the CSA may be decreased, if the subject's plasma concentration of the CSA, determined after administration of the first dose level of the CSA has started, is greater than a second threshold concentration (e.g., about 750 ng/mL). A dose level of the CSA may be maintained, if the subject's plasma concentration of the CSA, determined after administration of the first dose level of the CSA has started, is greater than or equal to a first threshold concentration and less than or equal to a second threshold concentration (e.g., between about 300 ng/mL and about 750 ng/mL). Treatment methods described herein are effective to achieve a target plasma concentration range and dose in a single step following a single plasma concentration determination after administration of the first dose level of the CSA has started. Benefits of such treatment methods may include, but are not limited to, large proportion of patients achieving the target plasma concentration range with the initial dose, fewer barriers and better patient compliance in achieving dose optimization, shorter period of time to reach target plasma concentration range and an effective dose, and minimizing toxicity issues. The treatment method described herein strikes an unexpected balance between safety and efficacy, especially for patients who may not receive an adjusted second dose level of the CSA.

In a phase 3 clinical trial, Global Approach to Lowering Adverse Cardiac Outcomes through Improving Contractility in Heart Failure (GALACTIC-HF), the following dosing regimen was used to assess treatment effect with omecamtiv mecarbil in patients with heart failure with reduced ejection fraction. At the initiation of treatment, a first dose level of 25 mg twice daily was orally administered to subjects randomized to receive omecamtiv mecarbil. At study visit week 2, a predose blood sample was collected. At week 4, subjects with week 2 omecamtiv mecarbil predose plasma concentration of less than 200 ng/mL would increase their dose level to 50 mg twice daily; subjects with week 2 plasma concentrations greater than or about 200 ng/mL but less than 300 ng/mL would increase their dose level to 37.5 mg twice daily; subjects with week 2 plasma concentrations greater than or about 300 ng/mL but less than 1000 ng/mL would maintain a dose level of 25 mg twice daily; and subjects with plasma concentration greater than or about 1000 ng/mL would start administration of placebo twice daily. At weeks 6, a predose blood sample was collected to confirm plasma concentration achieved and assess if changes to the dose should be made. It was found that at week 12, among the patients who were assigned to receive omecamtiv mecarbil twice daily, 28.9% were receiving the 25 mg dose, 13.6% the 37.5 mg dose, and 47.6% the 50 mg dose. The dosing regimen used in the GALACTIC-HF study was associated with reduced risk of heart failure outcomes and a very low incidence of excessive concentrations of omecamtiv mecarbil (e.g., plasma concentration over 1000 ng/mL). Treatment results were described in, for example, Cardiac Myosin Activation with Omecamtiv Mecarbil in Systolic Heart Failure (Teerlink et al., N. Engl. J. Med., 2021, 384; 2) and NCT02929329.

Omecamtiv mecarbil has a narrow therapeutic window in the treatment of heart failure, where the maximum safe dose is relatively close to the minimum effective dose. The target plasma concentration range as described herein (e.g., a target plasma concentration from about 300 ng/mL to about 750 ng/mL) is important for safety and efficacy. If the subject's plasma concentration of omecamtiv mecarbil is too low, effective treatment might not be achieved. If the subject's plasma concentration of omecamtiv mecarbil is too high, serious adverse events, such as myocardial infarction or myocardial ischemia, could occur. At plasma concentrations exceeding 1200 ng/mL, the risk of cardiac ischemic events is increased, likely due to shortening of diastole and decreased coronary perfusion. In order to avoid excessive plasma concentration levels, previous Phase 2 and 3 clinical trials, such as the GALACTIC-HF study, employed dosing regimens in which patients began at the lowest dose level (e.g., 25 mg twice daily). Only after a determination of steady state plasma concentration would a patient be moved to a higher dose level if it was determined that this was appropriate to achieve sufficient efficacy. Furthermore, some patients would require a second dose adjustment to achieve a suitable plasma concentration of the drug. As described herein, it has been surprisingly determined that a treatment protocol in which patients begin at an intermediate dose level (e.g., 37.5 mg twice daily) can provide for safe administration of omecamtiv mecarbil, and such treatment protocols can have additional benefits for efficacy and patient compliance.

The treatment method described herein comprises an intermediate first dose level, for example, 37.5 mg twice daily, at least 30 mg twice daily, or 30 to 40 mg twice daily, and is effective to achieve a target plasma concentration range of about 300 ng/mL to about 750 ng/mL after a single plasma concentration determination. As described herein, starting at a greater first dose level compared to previous Phase 2 and 3 clinical trials was surprisingly determined to be suitable for achieving sufficient safety despite the narrow therapeutic window of omecamtiv mecarbil. Employing a treatment protocol that begins with an intermediate first dose level (e.g., 37.5 mg twice daily) has advantages of taking shorter time, for example, no more than 4 weeks, for a patient to receive a dose level effective to achieve the target plasma concentration range with minimum toxicity concern. For example, employing a treatment protocol that begins with 37.5 mg twice daily, a majority of patients (e.g., about 75% of patients) may achieve Cmax therapeutic concentrations of omecamtiv mecarbil (e.g., 300-750 ng/mL) in about 2 weeks In some embodiments, it is expected that about one third of these patients may maintain the first dose level, about two thirds may up-titrate to a higher dose level, and only a very small percentage (e.g., about 0.4%) may down-titrate to a lower dose level.

By starting patients at an intermediate dose level, patients will generally achieve the target plasma concentration following a single plasma concentration determination for dose adjustment, rather than requiring two rounds of concentration determination for dose adjustment, thereby reducing the testing burden on patients and increasing patient compliance by simplifying the protocol. Moreover, for patients who start treatment with the first dose level but do not receive a dose adjustment due to, for example, lack of patient follow-up to determine plasma concentration or other administrative barriers, these patients can still have the benefit of a safe and sufficiently effective treatment. It was previously observed that among patients who started at the dose level of 25 mg twice daily, many of them were at the highest dose level of 50 mg twice daily at week 12. This suggests that patients who remain on the 25 mg twice daily dose because they fail to return for dose adjustment or other administrative barriers may in many cases be receiving a dose that is outside of the target plasma concentration range and far below their maximally efficacious dose. By starting patients at an intermediate dose (e.g., 37.5 mg twice daily), patients who do not return for dose adjustment will be receiving an amount that is closer to their maximally efficacious dose. Contrary to prior clinical trials, it has now been determined that patients can be started safely at such an intermediate dose level.

In addition, dose adjustment based on a first threshold concentration (e.g., about 300 ng/mL) and a second threshold concentration (e.g., about 750 ng/mL) could provide more accuracy in the determination of subsequent dose level with minimum number of blood tests, especially for patients receiving a second dose level of 50 mg twice daily.

Definitions

As used in the present specification, the following words and phrases are generally intended to have the meanings as set forth below, except to the extent that the context in which they are used indicates otherwise.

Reference to "about" a value or parameter herein includes (and describes) that value or parameter per se, and any value or parameter 5% above or 5% below said parameter. For example, description to "about X" includes description of "X" and "X+/−5%".

"NYHA classification" or "NYHA class" refers to the New York Heart Association functional classification of heart failure symptoms. Descriptions of each of NYHA classes I, II, III, and IV can be found in "Classes of Heart Failure", American Heart Association, adapted from: 1) Dolgin M, Association NYH, Fox A C, Gorlin R, Levin R I, New York Heart Association. Criteria Committee. "Nomenclature and criteria for diagnosis of diseases of the heart and great vessels". 9th ed. Boston, MA: Lippincott Williams and Wilkins; Mar. 1, 1994; and 2) Criteria Committee, New York Heart Association, Inc. Diseases of the Heart and Blood Vessels. Nomenclature and Criteria for diagnosis, 6th edition Boston, Little, Brown and Co. 1964, p 114. Briefly, NYHA class I indicates that the patient has no limitation of physical activity; ordinary physical activity does not cause undue fatigue, palpitation, dyspnea (shortness of breath). NYHA class II indicates that the patient has slight limitation of physical activity; comfortable at rest; ordinary physical activity results in fatigue, palpitation, dyspnea (shortness of breath). NYHA class III indicates that the patient has marked limitation of physical activity; comfortable at rest; less than ordinary physical activity causes fatigue, palpitation, or dyspnea. NYHA class IV indicates that the patient is unable to carry on any physical activity without discomfort; symptoms of heart failure at rest; if any physical activity is undertaken, discomfort increases.

The term "pharmaceutically acceptable salt" refers to a salt of any of the compounds herein that are known to be non-toxic and are commonly used in the pharmaceutical literature. In some embodiments, the pharmaceutically acceptable salt of a compound retains the biological effectiveness of the compounds described herein and are not biologically or otherwise undesirable. Examples of pharmaceutically acceptable salts can be found in Berge et al., Pharmaceutical Salts, *J. Pharmaceutical Sciences*, January 1977, 66(1), 1-19. Pharmaceutically acceptable acid addition salts can be formed with inorganic acids and organic acids. Inorganic acids from which salts can be derived include, for example, hydrochloric acid, hydrobromic acid, sulfuric acid, nitric acid, and phosphoric acid. Organic acids from which salts can be derived include, for example, acetic acid, propionic acid, glycolic acid, pyruvic acid, lactic acid, oxalic acid, malic acid, maleic acid, malonic acid, succinic acid, fumaric acid, tartaric acid, citric acid, benzoic acid, cinnamic acid, mandelic acid, methanesulfonic acid, ethanesulfonic acid, 2-hydroxyethylsulfonic acid, p-toluenesulfonic acid, stearic acid and salicylic acid. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, and aluminum. Organic bases from which salts can be derived include, for example, primary, secondary, and tertiary amines; substituted amines including naturally occurring substituted amines; cyclic amines; and basic ion exchange resins. Examples of organic bases include isopropylamine, trimethylamine, diethylamine, triethylamine, tripropylamine, and ethanolamine. In some embodiments, the pharmaceutically acceptable base addition salt is selected from ammonium, potassium, sodium, calcium, and magnesium salts.

If the compound described herein is obtained as an acid addition salt, the free base can be obtained by basifying a solution of the acid salt. Conversely, if the compound is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds (see, e.g., Berge et al., Pharmaceutical Salts, *J. Pharmaceutical Sciences*, January 1977, 66(1), 1-19). Those skilled in the art will recognize various synthetic methodologies that may be used to prepare pharmaceutically acceptable addition salts.

The term "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in pharmaceutical compositions is contemplated. Supplementary active ingredients can also be incorporated into the pharmaceutical compositions.

The terms "patient," "individual," and "subject" refer to an animal, such as a mammal. Mammals include, for example, mice, rats, dogs, cats, pigs, sheep, horses, cows and humans. In some embodiments, the patient or subject is a human, for example a human that has been or will be the object of treatment, observation or experiment. The compounds, compositions and methods described herein can be useful in both human therapy and veterinary applications.

"Treatment" (and related terms, such as "treat", "treated", "treating") includes one or more of: inhibiting a disease or disorder; slowing or arresting the development of clinical symptoms of a disease or disorder; and/or relieving a disease or disorder (i.e., causing relief from or regression of clinical symptoms). The term covers both complete and partial reduction or prevention of the condition or disorder, and complete or partial reduction of clinical symptoms of a disease or disorder. Thus, compounds described and/or disclosed herein may prevent an existing disease or disorder from worsening, assist in the management of the disease or disorder, or reduce or eliminate the disease or disorder.

Reference to any dose amount of a compound or pharmaceutically acceptable salt thereof described herein (e.g., 25 mg, 37.5 mg, 50 mg, etc. of omecamtiv mecarbil) refers to the amount (e.g., equivalent mass) of said compound without any salt (e.g., omecamtiv mecarbil anhydrous free base).

Cardiac Sarcomere Activators (CSA)

In some embodiments, a CSA induces the activation of by, e.g., sensitizing cardiac myofilaments to $Ca^{2+}$, activating troponin or tropomyosin, or directly activating the cardiac myosin. In some embodiments, a CSA promotes sarcomere responsiveness to calcium ($Ca^{2+}$). In some embodiments, the CSA is omecamtiv mecarbil or a pharmaceutically acceptable salt (e.g., omecamtiv mecarbil hydrochloride salt) or a pharmaceutically acceptable hydrate of a pharmaceutically acceptable salt (e.g., omecamtiv mecarbil dihydrochloride hydrate).

Omecamtiv Mecarbil (OM)

Omecamtiv mecarbil, also known as CK-1827452 or AMG 423, is a first in class direct activator of cardiac myosin that directly targets the contractile mechanisms of cardiac myocytes intended to enhance efficiency of myocardial contraction in patients suffering from a cardiovascular condition, such as heart failure. The free base of omecamtiv mecarbil is described chemically as methyl 4-(2-fluoro-3-(3-(6-methylpyridin-3-yl)ureido)benzyl)piperazine-1-carboxylate having the structural formula:

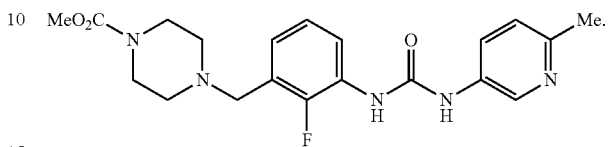

Omecamtiv mecarbil is disclosed in U.S. Pat. No. 7,507,735 titled "Compounds, Compositions and Method", the entirety of which is incorporated herein by reference. Description of omecamtiv mecarbil and method of making omecamtiv mecarbil can be found in, e.g., Example 3 column 55 and 56 of the above referenced patent.

Omecamtiv mecarbil was the subject of several Phase 2 clinical trials, including Chronic Oral Study of Myosin Activation to Increase Contractility in Heart Failure (COSMIC-HF), which evaluated omecamtiv mecarbil in patients with chronic heart failure and left ventricular systolic dysfunction (see, e.g., NCT01786512). Global Approach to Lowering Adverse Cardiac Outcomes Through Improving Contractility in Heart Failure (GALACTIC-HF), was a Phase 3 global cardiovascular outcomes study, which demonstrated a statistically significant effect of treatment with omecamtiv mecarbil to reduce risk of the primary composite endpoint of cardiovascular death or heart failure events compared to placebo in patients treated with standard of care (see, e.g., NCT02929329).

Omecamtiv mecarbil may be in the form of a salt or a hydrate of a salt, such as omecamtiv mecarbil dihydrochloride hydrate or omecamtiv mecarbil dihydrochloride monohydrate. The molecular formula of omecamtiv mecarbil dihydrochloride hydrate is $C_{20}H_{24}FN_5O_3$-2HCl—$H_2O$, with a relative molecular weight of 492.37 g/mol. In some embodiments, omecamtiv mecarbil is in the form of a base (e.g., omecamtiv mecarbil anhydrous free base). In some embodiments, omecamtiv mecarbil is in the form of a salt (e.g., omecamtiv mecarbil hydrochloride salt). In some embodiments, omecamtiv mecarbil is in the form of a salt hydrate (e.g., omecamtiv mecarbil dihydrochloride monohydrate). Omecamtiv mecarbil dihydrochloride salt forms are disclosed in U.S. Pat. No. 9,988,354 titled "Salt of Omecamtiv Mecarbil and Process for Preparing Salt", the entirety of which in incorporated herein by reference. Other salts or crystalline forms of omecamtiv mecarbil are described in, for example, WO2020011626 titles "Crystalline 2-fluoro-3-nitrotoluene and process for the preparation thereof", WO2020014406 titled "Solid state forms of omecamtiv mecarbil & omecamtiv mecarbil dihel", WO2021070123 titled "Solid forms of omecamtiv mecarbil dihydrochloride and processes thereof", WO2021053175 titled "Salts of omecamtiv mecarbil and solid forms thereof", WO2021053189 titled "Salts of omecamtiv mecarbil and solid forms thereof", WO2021136477 titled "Cocrystal of dihydrochloride of compound i and preparation method therefor and use thereof", and WO2021070124 titled "Alternate processes for the preparation of omecamtiv mecarbil".

A pharmaceutical formulation of omecamtiv mecarbil for oral administration is disclosed in U.S. Pat. No. 9,951,015 titled "Heterocyclic Compounds and Their Uses", the entirety of which is incorporated herein by reference.

Methods

Described herein are methods of treating heart failure in a subject in need thereof using a cardiac sarcomere activator (CSA). In some embodiments, the treatment comprises a) administering to the subject a first dose level of a cardiac sarcomere activator (CSA) for an initial period of time; and b) administering to the subject a second dose level of the CSA for a second period of time based on the subject's plasma concentration of the CSA determined after administration of the first dose level of the CSA has started; wherein: b-i) when the subject's plasma concentration of the CSA is less than a first threshold concentration, the second dose level of the CSA is greater than the first dose level of the CSA; b-ii) when the subject's plasma concentration of the CSA is greater than or equal to a first threshold concentration and less than or equal to a second threshold concentration, the second dose level of the CSA is the same as the first dose level of the CSA; and b-iii) when the subject's plasma concentration of the CSA is greater than a second threshold concentration, the second dose level of the CSA is less than the first dose level of the CSA; and wherein the CSA is omecamtiv mecarbil, or a pharmaceutically acceptable salt thereof, or a hydrate of any of the foregoing. In some embodiments, the treatment requires a single plasma concentration determination after the first administration of the first dose level of the CSA to determine the dose level of the CSA effective to achieve the target plasma concentration range.

Dose Level

In some embodiments, the treatment comprises administering to the subject a first dose level of the CSA of at least about 30 mg twice daily, e.g., 30 mg twice daily, 30.5 mg twice daily, 31 mg twice daily, 31.5 mg twice daily, 32 mg twice daily, 32.5 mg twice daily, 33 mg twice daily, 33.5 mg twice daily, 34 mg twice daily, 34.5 mg twice daily, 35 mg twice daily, 35.5 mg twice daily, 36 mg twice daily, 36.5 mg twice daily, 37 mg twice daily, 37.5 mg twice daily, 38 mg twice daily, 38.5 mg twice daily, 39 mg twice daily, 39.4 mg twice daily, and 40 mg twice daily, and a second dose level of the CSA. In some embodiments, the treatment comprises administering to the subject a first dose level of the CSA of from about 30 mg twice daily to about 40 mg twice daily, from about 30 mg twice daily to about 45 mg twice daily, from about 35 mg twice daily to about 40 mg twice daily, or from about 35 mg twice daily to about 45 mg twice daily, and a second dose level of the CSA. In some embodiments, the first dose level of the CSA is about 37.5 mg twice daily. In some embodiments, the second dose level of the CSA is less than the first dose level of the CSA (e.g., about 25 mg twice daily). In some embodiments, the second dose level of the CSA is the same as the first dose level of the CSA (e.g., about 37.5 mg twice daily). In some embodiments, the second dose level of the CSA is greater than the first dose level of the CSA (e.g., about 50 mg twice daily).

In some embodiments, the treatment comprises administering to the subject a first dose level of the CSA of at least about 30 mg twice daily, e.g., 30 mg twice daily, 30.5 mg twice daily, 31 mg twice daily, 31.5 mg twice daily, 32 mg twice daily, 32.5 mg twice daily, 33 mg twice daily, 33.5 mg twice daily, 34 mg twice daily, 34.5 mg twice daily, 35 mg twice daily, 35.5 mg twice daily, 36 mg twice daily, 36.5 mg twice daily, 37 mg twice daily, 37.5 mg twice daily, 38 mg twice daily, 38.5 mg twice daily, 39 mg twice daily, 39.4 mg twice daily, and 40 mg twice daily, a second dose level of the CSA, and a third dose level of the CSA. In some embodiments, the first dose level of the CSA is from about 30 mg twice daily to about 40 mg twice daily, from about 30 mg twice daily to about 45 mg twice daily, from about 35 mg twice daily to about 40 mg twice daily, or from about 35 mg twice daily to about 45 mg twice daily. In some embodiments, the third dose level of the CSA is less than the second dose level, for example, the third level of the CSA is about 37.5 mg twice daily, about 25 mg twice daily, or 25 mg once daily. In some embodiments, the third dose level of the CSA is greater than the second dose level, for example, the third dose level of the CSA is about 37.5 mg twice daily or 50 mg twice daily. In some embodiments, the third dose level of the CSA is the same as the second dose level, for example, the third dose level of the CSA is about 25 mg twice daily, about 37.5 mg twice daily, or about 50 mg twice daily.

Administration Period

In some embodiments, the treatment comprises administering to the subject a first dose level of the CSA of at least about 30 mg twice daily (e.g., 37.5 mg twice daily) for an initial period of time. In some embodiments, the initial period of time is at least about 2 weeks, e.g., 2 weeks, 2.5 weeks, 3 weeks, 3.5 weeks, 4 weeks, 4.5 weeks, 5 weeks, 5.5 weeks, and 6 weeks. In some embodiments, the initial period of time is 2 to 6 weeks, 2 to 5 weeks, 2 to 4 weeks, 3 to 6 weeks, 3 to 5 weeks, 3 to 4 weeks, 4 to 5 weeks, or 4 to 6 weeks. In some embodiments, the treatment comprises administering to the subject a first dose level of the CSA of from about 30 mg twice daily to about 40 mg twice daily, from about 30 mg twice daily to about 45 mg twice daily, from about 35 mg twice daily to about 40 mg twice daily, or from about 35 mg twice daily to about 45 mg twice daily for an initial period of time. In some embodiments, the initial period of time is about 4 weeks.

In some embodiments, the treatment further comprises administering to the subject a second dose level of the CSA for a second period of time based on the subject's plasma concentration of the CSA determined after administration of the first dose level of the CSA has started. In some embodiments, the second period of time is at least about 2 weeks, e.g., 2 weeks, 2.5 weeks, 3 weeks, 3.5 weeks, 4 weeks, 4.5 weeks, 5 weeks, 5.5 weeks, and 6 weeks. In some embodiments, the initial period of time is 2 to 6 weeks, 2 to 5 weeks, 2 to 4 weeks, 3 to 6 weeks, 3 to 5 weeks, 3 to 4 weeks, 4 to 5 weeks, 4 to 6 weeks, or for as long as treatment is recommended or efficacious.

In some embodiments, the treatment further comprises administering to the subject a third dose level of the CSA for a third period of time based on the subject's plasma concentration of the CSA determined after administration of the second dose level of the CSA has started. In some embodiments, the third period of time is at least about 2 weeks, e.g., 2 weeks, 2.5 weeks, 3 weeks, 3.5 weeks, 4 weeks, 4.5 weeks, 5 weeks, 5.5 weeks, and 6 weeks. In some embodiments, the initial period of time is 2 to 6 weeks, 2 to 5 weeks, 2 to 4 weeks, 3 to 6 weeks, 3 to 5 weeks, 3 to 4 weeks, 4 to 5 weeks, 4 to 6 weeks, or for as long as treatment is recommended or efficacious.

Plasma Concentration Determination

In some embodiments, the subject's plasma concentration of the CSA is determined within the initial period of time, e.g., at about 2 weeks after the first administration of the first dose level of the CSA, at about 3 weeks after the first administration of the first dose level of the CSA, or at about 4 weeks after the first administration of the first dose level of the CSA. In some embodiments, the subject's plasma concentration of the CSA is determined at about 2 to 4 weeks after the first administration of the first dose level of the CSA. In some embodiments, the subject's plasma concentration of the CSA is determined at about 2 weeks after the first administration of the first dose level of the CSA.

In some embodiments, the treatment requires only one plasma concentration determination after the first administration of the first dose level of the CSA and the second dose level of the CSA is determined based on the subject's plasma concentration of the CSA. In some embodiments, when the subject's plasma concentration of the CSA is less than a first threshold concentration, the second dose level of the CSA is greater than the first dose level of the CSA; when the subject's plasma concentration of the CSA is greater than or equal to a first threshold concentration and less than or equal to a second threshold concentration, the second dose level of the CSA is the same as the first dose level of the CSA; and when the subject's plasma concentration of the CSA is greater than a second threshold concentration, the second dose level of the CSA is less than the first dose level of the CSA. In some embodiments, the first threshold concentration is from about 200 ng/mL to about 300 ng/mL. In some embodiments, the first threshold concentration is about 300 ng/mL. In some embodiments, the second threshold concentration is from about 750 ng/mL to about 1000 ng/mL, or from about 750 ng/mL to about 800 ng/mL. In some embodiments, the second threshold concentration is about 750 ng/mL. In some embodiments, treatment is effective to achieve a target plasma concentration range of about 300 ng/mL to about 750 ng/mL. In some embodiments, the target plasma concentration range is achieved after administering to the subject the first dose level of the CSA, for a first period of time (e.g., at least 2 weeks). In some embodiment, no dose change is needed after the administration of the first dose level. In some embodiments, the target plasma concentration range is achieved after administering to the subject a second dose level of the CSA. In some embodiments, the target plasma concentration range is achieved after administering to the subject a second dose level of the CSA for a second period of time (e.g., at least 2 weeks). In some embodiments, the second dose level of the CSA is effective to achieve the target plasma concentration range. In some embodiment, no further dose adjustment is needed after the administration of the second dose level.

In some embodiments, the treatment may include a second plasma concentration determination within the second period of time and a third dose level of the CSA is determined based on the subject's second plasma concentration of the CSA. In some embodiments, the second plasma concentration is determined at about 6 weeks or at least about 6 weeks after the first administration of the first dose level of the CSA, at about 7 weeks after the first administration of the first dose level of the CSA, or at about 8 weeks after the first administration of the first dose level of the CSA. In some embodiments, the subject's second plasma concentration of the CSA is determined at about 6 to 8 weeks after the first administration of the first dose level of the CSA. In some embodiments, the subject's plasma concentration of the CSA is determined at about 2 weeks after the first administration of the second dose level of the CSA.

Dose Adjustment

In some embodiments, the treatment comprises a) administering to the subject a first dose level of a cardiac sarcomere activator (CSA) of about 37.5 mg twice daily for an initial period of time; and b) administering to the subject a second dose level of the CSA for a second period of time based on the subject's plasma concentration of the CSA determined after administration of the first dose level of the CSA has started; wherein: b-i) when the subject's plasma concentration of the CSA is less than 300 ng/mL, the second dose level of the CSA is about 50 mg twice daily; b-ii) when the subject's plasma concentration of the CSA is greater than or equal to 300 ng/mL and less than or equal to 750 ng/ml, the second dose level of the CSA is about 37.5 mg twice daily; and b-iii) when the subject's plasma concentration of the CSA is greater than 750 ng/ml, the second dose level of the CSA is about 25 mg twice daily; and wherein the CSA is omecamtiv mecarbil, or a pharmaceutically acceptable salt thereof, or a hydrate of any of the foregoing.

In some embodiments, the first dose level of the CSA is about 37.5 mg twice daily and the initial period of time is about 4 weeks. In some embodiments, the first dose level of the CSA is about 37.5 mg twice daily, the initial period of time is about 4 weeks, and the subject's plasma concentration of the CSA is determined at about 2 weeks after the first administration of the first dose level of the CSA. In some embodiments, the first dose level of the CSA is about 37.5 mg twice daily, the initial period of time is about 4 weeks, the subject's plasma concentration of the CSA is determined at about 2 weeks after the first administration of the first dose level of the CSA, and the second period of time is at least about 2 weeks. In some embodiments, the first dose level of the CSA is about 37.5 mg twice daily and the second dose level of the CSA is about 50 mg twice daily. In some embodiments, the first dose level of the CSA is about 37.5 mg twice daily and the second dose level of the CSA is about 37.5 mg twice daily. In some embodiments, the first dose level of the CSA is about 37.5 mg twice daily and the second dose level of the CSA is about 25 mg twice daily.

In some embodiments, the first dose level of the CSA is about 37.5 mg twice daily, the initial period of time is about 4 weeks, the subject's plasma concentration of the CSA is determined at about 2 weeks after the first administration of the first dose level of the CSA, the second period of time is at least about 2 weeks, and the second dose level of the CSA is about 50 mg twice daily. In some embodiments, the first dose level of the CSA is about 37.5 mg twice daily, the initial period of time is about 4 weeks, the subject's plasma concentration of the CSA is determined at about 2 weeks after the first administration of the first dose level of the CSA, the second period of time is at least about 2 weeks, and the second dose level of the CSA is about 37.5 mg twice daily. In some embodiments, the first dose level of the CSA is about 37.5 mg twice daily, the initial period of time is about 4 weeks, the subject's plasma concentration of the CSA is determined at about 2 weeks after the first administration of the first dose level of the CSA, the second period of time is at least about 2 weeks, and the second dose level of the CSA is about 25 mg twice daily.

In some embodiments, the second dose level of the CSA is 50 mg twice daily and it is administered to the subject at about 2 to 4 weeks (e.g. at 2 weeks, at about 3 weeks, or at about 4 weeks) after the first administration of the first dose level, when the subject's plasma concentration of the CSA is less than 300 ng/mL determined at about 2 to 4 weeks (e.g. at 2 weeks, at about 3 weeks, or at about 4 weeks) after the first administration of the first dose level (e.g., 37.5 mg twice daily). In some embodiments, no further dose adjustment is required following the administration of the second dose level.

In some embodiments, the treatment further comprises c) administering to the subject a third dose level of the CSA for a third period of time based on the subject's second plasma concentration of the CSA determined after administration of the second dose level of the CSA has started. In some embodiments, when the subject's second plasma concentration of the CSA is less than a first threshold concentration, the third dose level of the CSA is greater than the second dose level of the CSA; when the subject's second plasma concentration of the CSA is greater than or equal to a first threshold concentration and less than or equal to a second threshold concentration, the third dose level of the CSA is the same as the second dose level of the CSA; and when the subject's second plasma concentration of the CSA is greater than a second threshold concentration, the third dose level of the CSA is less than the second dose level of the CSA. In some embodiments, the third dose level of the CSA is 25 mg twice daily.

In some embodiments, the subject's second plasma concentration of the CSA is determined at about 2 to 4 weeks after the first administration of the second dose level of the CSA. In some embodiments, the subject's second plasma concentration of the CSA is determined at about 6 to 8 weeks after the first administration of the first dose level of the CSA. In some embodiments, the third dose level of the CSA is greater than the second dose level. In some embodiments, the third dose level of the CSA is the same as the second dose level. In some embodiments, the third dose level of the CSA is less than the second dose level. In some embodiments, the third dose level of the CSA is 37.5 mg twice daily. In some embodiments, the third dose level of the CSA is 50 mg twice daily.

In some embodiments the method results in an increase of the time to a heart failure event, cardiovascular death, left ventricular assist device (LVAD) implantation/cardiac transplant, or stroke, whichever occurred first, in patients. In some embodiments the method results in an increase of the time to a heart failure event, cardiovascular death, left ventricular assist device (LVAD) implantation/cardiac transplant, or a stroke, in patients. In some embodiments the method results in an increase of the time to a stroke, in patients.

Subject

Subjects with more severe symptoms of heart failure may receive greater benefit with the treatment methods described herein. In some embodiments, the subject has a low Left ventricular EF (LVEF), such as about 40% or lower (e.g., about 40%, about 39%, about 38%, about 37%, or about 36%), or about 39% or lower, or about 38% or lower, or about 37% or lower, or about 36% or lower, or about 35% or lower (e.g., about 35%, about 34%, about 33%, about 32%, about 31%), or about 34% or lower, or about 33% or lower, or about 32% or lower, or about 31% or lower, or about 30% or lower, or about 29% or lower, or about 28% or lower, or about 27% or lower, or about 26% or lower, or about 25% or lower, or about 24% or lower, or about 23% or lower, or about 22% or lower. In some embodiments, in conjunction with embodiment above or below, the subject has a LVEF of about 30%, about 29%, about 28%, about 27%, about 26%, about 25%, about 24%, about 23%, about 22%, about 21%, about 20%, about 19%, about 18%, about 17%, about 16%, about 15%, about 14%, about 13%, about 12%, about 11%, or about 10%. In some embodiments, the subject has a LVEF of less than 40%. In some embodiments, the subject has a LVEF of less than 35%. In some embodiments, the subject has a LVEF of less than 30%. In some embodiments, the subject has a LVEF of less than 28%. In some embodiments, the subject has a LVEF of less than 25%. In some embodiments, the subject has a LVEF of less than 22%. In some embodiments, the subject has a left ventricular ejection fraction of about 30% or lower.

In some embodiments, the LVEFs described herein are associated with subjects without atrial fibrillation or flutter. In some embodiments, the LVEFs described herein are associated with subjects with atrial fibrillation or flutter. For example, in some embodiments, the subject has a Left ventricular EF (LVEF) <40% without atrial fibrillation or flutter. In some embodiments, the subject has a Left ventricular EF (LVEF) <35% without atrial fibrillation or flutter. In some embodiments, the subject has a Left ventricular EF (LVEF) <30% without atrial fibrillation or flutter. In some embodiments, the subject has a LVEF <35% with atrial fibrillation or flutter. In some embodiments, the subject has a LVEF <30% with atrial fibrillation or flutter. In some embodiments, the subject has a LVEF <25% with atrial fibrillation or flutter. In some embodiments, in conjunction with embodiments above or below, the subject is taking digoxin. In some embodiments, in conjunction with embodiments above or below, the subject is not taking digoxin.

In some embodiments, in conjunction with embodiments above or below, the subject has high NT-proBNP level, such as at least about 1000 pg/mL (e.g., 1000, 1100, 1200, 1300, 1400, 1500, 1600, 1700, 1800, and 1900 pg/mL), at least about 2000 pg/mL (e.g., 2000, 2100, 2200, 2300, and 2400 pg/mL), at least about 2500 pg/mL (e.g., 2500, 2600, 2700, 2800, and 2900 pg/mL), or at least 3000 pg/mL (e.g., 3000, 3500, 4000, 4500, 5000, 5500, 6000, 7000, 8000, 9000, 10,000, 15,000, and 20,000 pg/ml). In some embodiments, the subject has NT-proBNP level of at least about 1500 pg/mL. In some embodiments, the subject has NT-proBNP level of at least about 2000 pg/mL. In some embodiments, the subject has NT-proBNP level of at least about 2500 pg/mL. In some embodiments, the subject has NT-proBNP level of at least about 3000 pg/mL.

In some embodiments, the NT-proBNP levels described herein are associated with subjects without atrial fibrillation or flutter. In some embodiments, the NT-proBNP levels described herein are associated with subjects with atrial fibrillation or flutter. For example, in some embodiments, the subject has N-terminal pro-B-type natriuretic peptide (NT-proBNP) ≥2000 pg/ml without atrial fibrillation or flutter. In some embodiments, the subject has NT-proBNP ≥3000 pg/mL with atrial fibrillation or flutter.

In some embodiments, the subject is currently hospitalized or has had one or more HF hospitalizations within 12 months. In some embodiments, the subject is currently hospitalized or has had one or more HF hospitalizations within 6 months. In some embodiments, the subject is currently on a loop diuretic, such as furosemide, bumetanide, torsemide, or ethacrynic acid. In some embodiments, the subject has chronic heart failure, or a New York Heart Association Class II or III heart failure. In some embodiments, the subject does not receive dose adjustment and is administered a first dose level of the CSA only.

EXAMPLES

The application may be better understood by reference to the following non-limiting examples, which are provided as exemplary embodiments of the application. The following examples are presented in order to more fully illustrate embodiments and should in no way be construed, however, as limiting the broad scope of the application. While certain embodiments of the present application have been shown and described herein, it will be obvious that such embodiments are provided by way of example only. Numerous variations, changes, and substitutions may occur to those skilled in the art without departing from the spirit and scope of the invention. It should be understood that various alternatives to the embodiments described herein may be employed in practicing the methods described herein.

The following abbreviations are used in the Examples: ACEi refers to angiotensin-converting enzyme inhibitor; ARB refers to angiotensin receptor blocker; ARNi refers to angiotensin receptor-neprilysin inhibitor; BB refers to beta blocker; CRT refers to cardiac resynchronization therapy; ED refers to emergency department; eGFR refers to estimated glomerular filtration rate; HF refers to heart failure; hsTn refers to high-sensitivity troponin I; ICD refers to implantable cardioverter-defibrillator; KCCQ refers to Kansas City Cardiomyopathy Questionnaire; LVEF refers to left ventricular ejection fraction; MAGGIC refers to Meta-Analysis Global Group in Chronic HF; MRA refers to mineralocorticoid receptor antagonist; NEJM refers to The New England Journal of Medicine; NT-proBNP refers to N-terminal pro-B-type natriuretic peptide; NYHA refers to New York Heart Association; SBP refers to systolic blood pressure; and SGLT2 refers to sodium-glucose co-transporter 2.

The endpoints of studies and event definitions were based on ACC/AHA standards for endpoint definitions in cardiovascular clinical trials as described in Hicks et al. 2017 Cardiovascular and Stroke Endpoint Definitions for Clinical Trials, J Am Coll Cardiol 2018; 71:1021-34.

Example 1—GALACTIC-HF Clinical Trial

In a phase 3 clinical trial, Global Approach to Lowering Adverse Cardiac Outcomes through Improving Contractility in Heart Failure (GALACTIC-HF), all eligible participants were randomized 1:1 to oral administration of either placebo or omecamtiv mecarbil (pharmacokinetic-guided dosing: 25, 37.5 or 50 mg) twice daily. Pre-dose plasma concentrations of omecamtiv mecarbil were measured at weeks 2 and 6 with respective dose adjustments on weeks 4 and 8. The patient and investigator were blinded to the plasma concentrations and dispensed dose. The full schedule of assessments is provided in the protocol available at NEJM.org and is summarized in Table 1.

TABLE 1

| Study Visit | Week 2 Plasma Concentration (ng/ml) | Current Dose BID | New Dose BID |
|---|---|---|---|
| Week 4 | <200 | 25 mg | 50 mg |
| | ≥200-<300 | | 37.5 mg |
| | ≥300-<1000 | | No change |
| | ≥1000 | | placebo |

| Study Visit | Week 6 Plasma Concentration (ng/ml) | Current Dose BID | New Dose BID |
|---|---|---|---|
| Week 8 | <750 | Any | No change |
| | ≥750-<1000 | 25 mg | No change |
| | | 37.5 mg | 25 mg |
| | | 50 mg | 37.5 mg |
| | ≥1000 | 25 mg | Placebo |
| | | 37.5 mg | 25 mg |
| | | 50 mg | |

| Study Visit | Week 6 Plasma Concentration (ng/ml) | Current Dose | New Dose |
|---|---|---|---|
| Week 24 Week 48 Q 48 weeks Unscheduled | ≥1000 | Any | Withdraw IP |

BID = twice a day; IP = investigational product; Q 48 = every 48

Dose-Response Analysis

A PK-guided dosing algorithm used in the GALACTIC-HF trial is shown in FIG. 1. Participants randomized to omecamtiv mecarbil were started at the lowest dose of 25 mg twice daily. The dose was increased only in participants both adherent to the regimen and whose omecamtiv mecarbil plasma concentrations were below the target range of 300-750 ng/mL after steady state was achieved at Week 2. At the end of Week 8, 28.6% of participants were on 25 mg BID (including participants whose plasma concentration results were not available in time for any dose titration visit or participant compliance with dosing was not affirmatively documented by the investigator), which was higher than the anticipated proportion (4.1%) based on population PK modeling. In participants who completed the dosing algorithm as intended and were titrated to 37.5 or 50 mg BID, mean omecamtiv mecarbil plasma concentrations were higher than those in the 25 mg BID dose group. Participants titrated to doses of 37.5 or 50 mg BID tended to have reduced risk of the primary composite endpoint and cardiovascular death compared to those at a dose of 25 mg BID, as shown in Table 2 below.

TABLE 2 primary composite endpoint and CV death by titrated dose group using primary analysis cox model or adjusting for significant pre-specified baseline covariates

| Dose Group [mean [OM], (SD) ng/mL] | Treatment Groups (n/N) | Hazard Ratio | 95% CI | p-value |
|---|---|---|---|---|
| Primary Endpoint Planned Primary Analysis Cox Model | | | | |
| 25 mg BID [184, (121)] | OM (516/1,269) vs PBO (1,477/3,897) | 1.00 | 0.90, 1.10 | 0.98 |
| 37.5 mg BID [345, (134)] | OM (225/602) vs PBO (1,477/3,897) | 0.93 | 0.81, 1.08 | 0.35 |
| 50 mg BID [297, (138)] | OM (677/2,070) vs PBO (1,477/3,897) | 0.87 | 0.80, 0.96 | 0.003 |
| Cox Model Adjusting for Significant Baseline Covariates | | | | |
| 25 mg BID [184, (121)] | OM (516/1,269) vs PBO (1,477/3,897) | 0.93 | 0.84, 1.03 | 0.19 |
| 37.5 mg BID [345, (134)] | OM (225/602) vs PBO (1,477/3,897) | 0.90 | 0.78, 1.03 | 0.13 |
| 50 mg BID [297, (138)] | OM (677/2,070) vs PBO (1,477/3,897) | 0.89 | 0.81, 0.97 | 0.009 |

TABLE 2-continued primary composite endpoint and CV death by titrated dose group using primary analysis cox model or adjusting for significant pre-specified baseline covariates

| Dose Group<br>[mean [OM], (SD) ng/mL] | Treatment Groups (n/N) | Hazard Ratio | 95% CI | p-value |
|---|---|---|---|---|
| CV Death | | | | |
| Planned Primary Analysis Cox Model | | | | |
| 25 mg BID [184, (121)] | OM (284/1,269) vs PBO (707/3,897) | 1.18 | 1.02, 1.35 | 0.02 |
| 37.5 mg BID [345, (134)] | OM (110/602) vs PBO (707/3,897) | 1.00 | 0.81, 1.22 | 0.97 |
| 50 mg BID [297, (138)] | OM (333/2,070) vs PBO (707/3,897) | 0.91 | 0.80, 1.04 | 0.15 |
| Cox Model Adjusting for Significant Baseline Covariates | | | | |
| 25 mg BID [184, (121)] | OM (284/1,269) vs PBO (707/3,897) | 1.11 | 0.97, 1.28 | 0.13 |
| 37.5 mg BID [345, (134)] | OM (110/602) vs PBO (707/3,897) | 0.94 | 0.77, 1.16 | 0.58 |
| 50 mg BID [297, (138)] | OM (333/2,070) vs PBO (707/3,897) | 0.98 | 0.86, 1.12 | 0.79 |

BID = twice daily;
CI = confidence interval;
CV = cardiovascular;
OM = omecamtiv mecarbil;
[OM] = plasma concentration of OM;
n = number of participants with observed data;
N = number of participants;
PBO = placebo;
SD = standard deviation.

A summary of participants by dose group at Week 4 (dose selection determined by the Week 2 concentrations of omecamtiv mecarbil), at Week 8 (dose selection determined by the Week 6 concentrations of omecamtiv mecarbil), and the final dose at Week 12, is provided in Table 3. Overall, the proportions of participants receiving each of the omecamtiv mecarbil doses remained generally consistent over time. At the Week 8 visit, 3.0% of participants had their doses adjusted from 50 to 25 mg BID and 1.1% from 37.5 to 25 mg BID. As noted above, the majority of these down titrations were due to a missing plasma concentration of omecamtiv mecarbil (laboratory value not available in time or PK sample not obtained). Down titrations due to plasma concentrations of omecamtiv mecarbil exceeding 750 ng/mL occurred in only 9 (0.22%) participants: 8 participants in the 750 to <1,000 ng/mL range, and 1 participant with a plasma concentration of 1,004 ng/mL.

TABLE 3 summary of dose groups

| | Placebo (N = 4112) | Omecamtiv Mecarbil (N = 4120) |
|---|---|---|
| Dose at Week 4, n (%) | | |
| 25 mg BID | 0 (0.0) | 993 (24.1) |
| 37.5 mg BID | 0 (0.0) | 635 (15.4) |
| 50 mg BID | 0 (0.0) | 2,173 (52.7) |
| Discontinued IP | 164 (4.0) | 132 (3.2) |
| No IP box dispensed | 47 (1.1) | 50 (1.2) |
| Placebo | 3,766 (91.6) | 0 (0.0) |
| Visit did not occur | 135 (3.3) | 137 (3.3) |
| Dose at Week 8, n (%) | | |
| 25 mg BID | 0 (0.0) | 1,180 (28.6) |
| 37.5 mg BID | 0 (0.0) | 577 (14.0) |
| 50 mg BID | 0 (0.0) | 2,002 (48.6) |
| Discontinued IP | 265 (6.4) | 257 (6.2) |
| No IP box dispensed | 44 (1.1) | 44 (1.1) |
| Placebo | 3,724 (90.6) | 0 (0.0) |
| Visit did not occur | 79 (1.9) | 60 (1.5) |
| Final dose at Week 12, n (%) | | |
| 25 mg BID | 0 (0.0) | 1,192 (28.9) |
| 37.5 mg BID | 0 (0.0) | 559 (13.6) |
| 50 mg BID | 0 (0.0) | 1,961 (47.6) |
| Discontinued IP | 366 (8.9) | 347 (8.4) |
| No IP box dispensed | 26 (0.6) | 18 (0.4) |
| Placebo | 3,668 (89.2) | 0 (0.0) |
| Visit did not occur | 52 (1.3) | 43 (1.0) |

BID = twice a day; IP = investigational product.
Notes:
N = Number of participants randomized excluding study center 29002. n = Number of participants with observed data. Percentages are based on N. For "Discontinued IP," the discontinuation occurred before the visit. For "No IP box dispensed," the discontinuation occurred after the visit.

Example 2—Simulation of Scheduled Dose Titration

Provided in this example are simulations for one titration scheme with two populations. The titration scheme starts at 37.5 mg BID and titrates higher or lower depending on <300 or >750 ng/mL at weeks 2, 4, and 6. The two populations are a general HFrEF population and a subpopulation of subjects with left ventricular ejection fraction (LVEF) <30%, as defined in GALACTIC-HF. A population pharmacokinetic (PK) model of omecamtiv mecarbil was previously developed using data from 6 studies, including GALACTIC-HF (Population Pharmacokinetic Properties of Omecamtiv Mecarbil in Healthy Subjects and Patients With Heart Failure With Reduced Ejection Fraction, Cardiovasc. Pharmacol. 2022; 79:539-548). To investigate the effect of formulation on omecamtiv mecarbil PK, the population PK model was updated with healthy subjects' data from five Phase 1 studies that used the modified-release (MR) Phase 3 formulation, using the previously established population PK model as the starting point. Simulation results are used to determine the number and percentage of patients in pre-specified exposure categories at the end of each dose titration period.

The population PK model was used to simulate individual concentration-time profiles up to 12 weeks for 4500 virtual subjects either from the general HFrEF population or a subpopulation of subjects with LVEF <30%. All subjects for the simulations were taken from study GALACTIC-HF (N=3884). Subjects with missing body weight were assigned the typical value (80 kg) during simulations. A summary of populations is shown in Table 4A.

TABLE 4A

|  | Real Population (General) (N = 3884) | Real Population (LVEF <30%) (N = 2202) | Virtual Population (General) (N = 4500) | Virtual Population (LVEF <30%) (N = 4500) |
|---|---|---|---|---|
| Body Weight (kg) | | | | |
| Mean (SD) | 82.8 (20.7) | 81.7 (21.2) | 82.8 (20.4) | 82.0 (21.2) |
| Median (CV %) | 80.1 (25.0) | 78.9 (25.9) | 80.5 (24.6) | 79.0 (25.9) |
| [Min, Max] | [36.0, 261] | [38.5, 261] | [36.0, 261] | [38.5, 261] |
| Missing | 3 (0.1%) | 1 (0.0%) | 5 (0.1%) | 0 (0%) |
| Age (years) | | | | |
| Mean (SD) | 64.5 (11.3) | 63.2 (11.7) | 64.7 (11.1) | 63.0 (11.7) |
| Median (CV %) | 66.0 (17.5) | 65.0 (18.5) | 66.0 (17.2) | 64.0 (18.5) |
| [Min, Max] | [18.0, 89.0] | [20.0, 88.0] | [18.0, 89.0] | [20.0, 88.0] |
| MDRD eGFR (mL/min) | | | | |
| Mean (SD) | 64.3 (23.2) | 64.6 (23.2) | 63.6 (23.0) | 64.4 (23.1) |
| Median (CV %) | 62.6 (36.0) | 62.6 (35.9) | 61.9 (36.2) | 62.4 (36.0) |
| [Min, Max] | [14.4, 217] | [14.5, 217] | [14.5, 214] | [14.5, 217] |
| Formulation | | | | |
| MR Phase 3 Formulation | 3884 (100%) | 2202 (100%) | 4500 (100%) | 4500 (100%) |

The model included covariate effects with body weight as a covariate on both the clearance and central volume of distribution, renal impairment as a covariate on the clearance only, age as a covariate on central volume of distribution only, and drug formulation to both the first-order absorption rate and relative bioavailability. Model parameters are described in Table 4B and model equations for clearance, central volume of distribution, first-order absorption rate, and relative bioavailability are as follows:

$$CL/F_{cov} = CL/F \cdot \left(\frac{BW}{80}\right)^{\theta_6} \cdot \left(\frac{EGFR}{71}\right)^{\theta_7}$$

$$V2/F_{cov} = V2/F \cdot \left(\frac{AGE}{65}\right)^{\theta_8} \cdot \left(\frac{BW}{80}\right)^{\theta_9}$$

$$KA_{cov} = KA \cdot (1+\theta_{10})$$

$$F_{cov} = F \cdot (1+\theta_{11})$$

$CL/F_{cov}$, $V2/F_{cov}$, $KA_{cov}$, $F_{cov}$ are the typical values of apparent clearance, apparent central volume of distribution, first-order rate of absorption, and relative bioavailability, respectively, after accounting for covariates; CL and V2 are the apparent clearance and apparent central volume of distribution, respectively, for the reference values of body weight (80 kg), Modification of Diet in Renal Disease (MDRD) estimated glomerular filtration rate (eGFR; 71 mL/min), and age (65 years); and $\theta_6$, $\theta_7$, $\theta_8$, $\theta_9$, $\theta_{10}$, and $\theta_{11}$ represent the body weight effect on CL, the MDRD eGFR effect on CL, the age effect on V2, the body weight effect on B2, and the formulation effect on KA and F, respectively.

TABLE 4B

THETA values: (CL) 12.1, (V2) 224.6, (Q) 20.2, (V3) 213.2, (KA) 0.1, (CLBW) 0.4, (CLEGFR) 0.3, (V2AGE) 1.9, (V2BW) 2.1, (KAFORMN) 0.2, (FIFORMN) 0.1

TABLE 4B-continued

OMEGA values (CL, V2, V3, KA): 0.09, 0, 0, 0, 0, 1.32, 0, 0, 0, 0, 0.46, 0, 0, 0, 0, 0.16
SIGMA value: 0.0669816

Simulations in General Population

The statistical summaries for the simulation of virtual subjects in the general HF population and virtual subjects in the HF with LVEF <30% population undergoing the proposed titration scheme are shown in Table 4C and 4D, respectively, in which all virtual subjects started with a dose of 37.5 mg BID. For $C_{max}$ at week 2 in the general population, 75.0% of subjects achieved a plasma concentration of 300-750 ng/mL, and a further 18.3% of subjects achieved a plasma concentration of 200-300 ng/mL. For $C_{max}$ at week 2 in the LVEF <30% population, 76.3% of subjects exhibited a plasma concentration of 300-750 ng/mL, and a further 17.3% of subjects exhibited a plasma concentration of 200-300 ng/mL. In both the general population and the LVEF <30% population, only 0.1% of subjects exhibited a $C_{max}$ at week 2 of >1200 ng/mL. For $C_{min}$, at week 2, 32.5% of subjects in the general population and 33.1% of subjects in the LVEF <30% population exhibited a plasma concentration of 300-750 ng/mL and a further 37.2% of subjects in the general population and 37.1% of subjects in the LVEF <30% population exhibited a plasma concentration of 200-300 ng/mL, with none exceeding 1200 ng/mL in either population. At week 2, about one third of the subjects maintained the starting dose level of 37.5 mg BID (32.5% and 33.1% in the general and LVEF <30% populations, respectively), and about two thirds of the subjects up-titrated to the higher 50 mg BID dose level (67.2% and 66.6% in the general and LVEF <30% populations, respectively). In both populations, only 0.4% down-titrated to the lower dose level of 25 mg BID. At week 4, almost all subjects (99.7%) maintained the current dose level in both populations. The results of this simulation indicate that when patients are started at a dose of 37.5 mg BID, the majority of patients in both a general population and an LVEF <30% population are expected to be at a therapeutic or sub-therapeutic dose of OM by week 2, and by week 4 after one round of plasma concentration and dose adjustment, the vast majority of patients in both populations are expected to be at a therapeutic dose. Furthermore, this simulation indicates that the incidence of plasma concentrations exceeding 1200 ng/mL is expected to be extremely low for a dosing regimen starting at an intermediate dose of 37.5 mg BID.

TABLE 4C

General Population

| | Week 2 (N = 4500) | Week 4 (N = 4500) | Week 6 (N = 4500) | Week 12 (N = 4500) |
|---|---|---|---|---|
| $C_{min}$ (ng/ml) | | | | |
| <200 | 1349 (30.0%) | 583 (13.0%) | 557 (12.4%) | 550 (12.2%) |
| >=200 to <300 | 1674 (37.2%) | 1544 (34.3%) | 1471 (32.7%) | 1447 (32.2%) |
| >=300 to <750 | 1461 (32.5%) | 2344 (52.1%) | 2428 (54.0%) | 2452 (54.5%) |
| >=750 to <1000 | 14 (0.3%) | 25 (0.6%) | 38 (0.8%) | 47 (1.0%) |
| >=1000 to <1200 | 2 (0.0%) | 3 (0.1%) | 5 (0.1%) | 3 (0.1%) |
| >=1200 | 0 (0%) | 1 (0.0%) | 1 (0.0%) | 1 (0.0%) |
| $C_{max}$ (ng/ml) | | | | |
| <200 | 111 (2.5%) | 7 (0.2%) | 9 (0.2%) | 6 (0.1%) |
| >=200 to <300 | 822 (18.3%) | 193 (4.3%) | 197 (4.4%) | 194 (4.3%) |
| >=300 to <750 | 3373 (75.0%) | 3930 (87.3%) | 3886 (86.4%) | 3896 (86.6%) |
| >=750 to <1000 | 169 (3.8%) | 332 (7.4%) | 370 (8.2%) | 349 (7.8%) |
| >=1000 to <1200 | 19 (0.4%) | 30 (0.7%) | 33 (0.7%) | 45 (1.0%) |
| >=1200 | 6 (0.1%) | 8 (0.2%) | 5 (0.1%) | 10 (0.2%) |
| Regimen (Pre-Titration) | | | | |
| placebo | 0 (0%) | 0 (0%) | 0 (0%) | 0 (0%) |
| 25 mg QD | 0 (0%) | 0 (0%) | 1 (0.0%) | 1 (0.0%) |
| 25 mg BID | 0 (0%) | 16 (0.4%) | 13 (0.3%) | 13 (0.3%) |
| 37.5 mg BID | 4500 (100%) | 1461 (32.5%) | 1472 (32.7%) | 1473 (32.7%) |
| 50 mg BID | 0 (0%) | 3023 (67.2%) | 3014 (67.0%) | 3013 (67.0%) |
| Titration Change | | | | |
| down-titrate | 16 (0.4%) | 10 (0.2%) | 1 (0.0%) | 0 (0%) |
| maintain | 1461 (32.5%) | 4488 (99.7%) | 4499 (100.0%) | 4500 (100%) |
| up-titrate | 3023 (67.2%) | 2 (0.0%) | 0 (0%) | 0 (0%) |

TABLE 4D

LVEF <30% Population

| | Week 2 (N = 4500) | Week 4 (N = 4500) | Week 6 (N = 4500) | Week 12 (N = 4500) |
|---|---|---|---|---|
| $C_{min}$ (ng/ml) | | | | |
| <200 | 1324 (29.4%) | 589 (13.1%) | 529 (11.8%) | 556 (12.4%) |
| >=200 to ≤300 | 1671 (37.1%) | 1512 (33.6%) | 1519 (33.8%) | 1500 (33.3%) |
| >=300 to <750 | 1489 (33.1%) | 2370 (52.7%) | 2416 (53.7%) | 2390 (53.1%) |
| >=750 to <1000 | 14 (0.3%) | 27 (0.6%) | 32 (0.7%) | 50 (1.1%) |

TABLE 4D-continued

LVEF <30% Population

| | Week 2 (N = 4500) | Week 4 (N = 4500) | Week 6 (N = 4500) | Week 12 (N = 4500) |
|---|---|---|---|---|
| >=1000 to <1200 | 2 (0.0%) | 1 (0.0%) | 3 (0.1%) | 3 (0.1%) |
| >=1200 | 0 (0%) | 1 (0.0%) | 1 (0.0%) | 1 (0.0%) |
| $C_{max}$ (ng/mL) | | | | |
| <200 | 106 (2.4%) | 7 (0.2%) | 10 (0.2%) | 7 (0.2%) |
| >=200 to <300 | 779 (17.3%) | 211 (4.7%) | 186 (4.1%) | 200 (4.4%) |
| >=300 to <750 | 3433 (76.3%) | 3895 (86.6%) | 3900 (86.7%) | 3887 (86.4%) |
| >=750 to <1000 | 160 (3.6%) | 349 (7.8%) | 358 (8.0%) | 354 (7.9%) |
| >=1000 to <1200 | 19 (0.4%) | 33 (0.7%) | 36 (0.8%) | 42 (0.9%) |
| >=1200 | 3 (0.1%) | 5 (0.1%) | 10 (0.2%) | 10 (0.2%) |
| Regimen (Pre-Titration) | | | | |
| placebo | 0 (0%) | 0 (0%) | 0 (0%) | 0 (0%) |
| 25 mg QD | 0 (0%) | 0 (0%) | 0 (0%) | 0 (0%) |
| 25 mg BID | 0 (0%) | 16 (0.4%) | 10 (0.2%) | 10 (0.2%) |
| 37.5 mg BID | 4500 (100%) | 1489 (33.1%) | 1503 (33.4%) | 1501 (33.3%) |
| 50 mg BID | 0 (0%) | 2995 (66.6%) | 2987 (66.4%) | 2989 (66.4%) |
| Titration Change | | | | |
| down-titrate | 16 (0.4%) | 8 (0.2%) | 0 (0%) | 0 (0%) |
| maintain | 1489 (33.1%) | 4486 (99.7%) | 4498 (100.0%) | 4500 (100%) |
| up-titrate | 2995 (66.6%) | 6 (0.1%) | 2 (0.0%) | 0 (0%) |

Example 3—New Clinical Trial

Patient Eligibility

Patient eligibility requirements include the following criteria for inclusion. Participants must be aged ≥18 years and ≤85 years. Patients must have a history of chronic HF, defined as requiring treatment for HF for a minimum of 3 months prior to randomization. Patients must be on loop diuretics at time of screening. Patients without atrial fibrillation or flutter must have a Left Ventricular EF (LVEF) <30%. Patients with atrial fibrillation or flutter must have a LVEF <25%. LVEF must be confirmed by local echocardiogram or core laboratory echocardiogram performed within 6 months prior to screening, and at least 3 months after acute coronary syndrome (ACS), cardiac surgery, valve procedures, any coronary revascularization, and/or cardiac resynchronization therapy (CRT). Patients must be currently hospitalized or have ≥1 HF hospitalization within 12 months. Patients must be established on SoC therapies consistent with physician discretion and regional clinical practice guidelines. Patients with atrial fibrillation or flutter at randomization will be capped at 15% of study participants. Patients must have B-type natriuretic peptide (BNP) >300 pg/ml or N-terminal pro-BNP (NT-proBNP) >1000 pg/ml (for subjects with atrial fibrillation, the cut off levels are: BNP >900 pg/mL or NT-proBNP >3000 pg/mL at screening).

Patient eligibility requirements also include the following criteria for exclusion from the study. Patients with ACS, cardiac surgery, valve surgery, any coronary revascularization, and/or CRT within 3 months of randomization are excluded. Patients with atrial fibrillation or flutter on digoxin are excluded from the study. Patients admitted to long term care facility or hospice are excluded from the study. Patients with a projected survival of <12 months based on clinical judgement are excluded from the study. Patients currently using vasopressors, inotropes, or mechanical circulatory support are excluded from the study. Patients with previous solid organ transplant or intent to transplant (on transplant list) are excluded from the study. With some exceptions, patients with active or recent (<2 years, but with documented cure, or >5 years without recurrence) malignancy are excluded from the study. Patients with a current pregnancy, or planned pregnancy during the study period are excluded from the study. Patients with an inability to provide informed consent or to comply with study schedule are excluded from the study.

Study Procedures

A randomized, placebo-controlled, double-blind, parallel group, multicenter, pragmatic clinical outcomes study in subjects with high-risk HF (defined by EF<30%, NT-pro BNP ≥1000, and a heart failure event within the preceding 12 months) is performed. The study is event driven and concludes when approximately 850 primary composite events (cardiovascular death, first HF event, LVAD implantation, cardiac transplantation, or stroke) have occurred. The trial will be conducted at large, multi-center integrated health delivery networks in the United States, Canada, and Europe.

Using the electronic health record (EHR) participants are screened for eligibility criteria at clinical sites associated with large integrated healthcare delivery networks. Eligible participants sign electronic informed consent forms, after which they enter a screening period either in the inpatient or outpatient setting. At screening, all subjects should be established for at least 30 days on standard of care therapies for HFrEF consistent with regional clinical practice guidelines. Eligibility is confirmed via a local echocardiogram performed within 6 months of screening.

Figure 2:
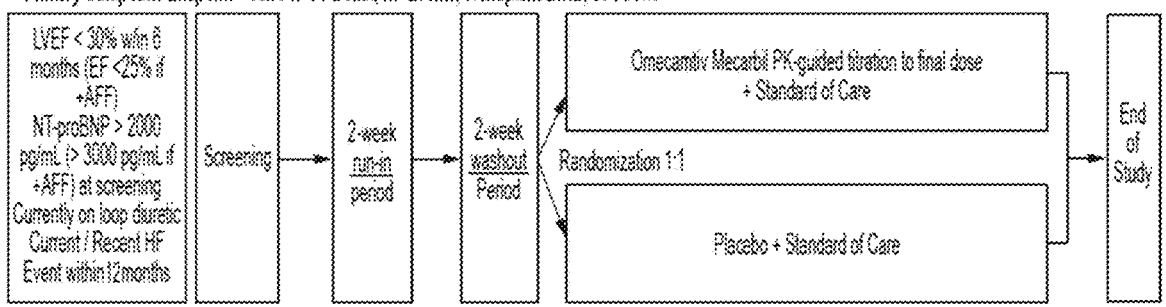
FIG. 2 shows a study protocol for clinical trial of omecamtiv mecarbil with starting dose of 37.5 mg twice daily

Approximately 1,800 screened subjects who meet all eligibility criteria are enrolled and randomized in a 1:1 ratio to omecamtiv mecarbil or placebo. Randomization is stratified by region and presence of AFF at baseline. The results are blinded to investigators. To evaluate medication tolerance and adherence prior to randomization, a run-in phase is conducted as follows: all participants are started on 37.5 mg twice daily. After two weeks, a pre-dose omecamtiv mecarbil plasma level is tested. Based on the results of this test, participants with an omecamtiv mecarbil level below the limit of quantification after two weeks of dosing are excluded from the study. The remaining participants are then to be randomized 1:1 to either placebo or their personalized dose of omecamtiv mecarbil (25 mg, 37.5 mg, or 50 mg) to achieve a target plasma concentration of 300 to 750 ng/mL. The investigational product is an omecamtiv mecarbil oral modified-release tablets in 25, 37.5, and 50 mg doses. A new supply of investigational product (IP) is administered to all subjects (OM and placebo) at the beginning of the run-in period, randomization, and week 2, regardless of randomized treatment cohort to maintain the blind. All participants and investigators are unaware of the dispensed dose. Post-randomization assessments are performed at weeks 2, 12, 24, 36, 48, and every 24 weeks thereafter, alternating remote and in-person visits. Endpoint adjudication occurs via the EHR by the local investigator with additional central adjudication of approximately 10% of events. A summary of the clinical trial design is provided in FIG. 2.

The administration of omecamtiv mecarbil or placebo will be temporarily suspended if the patient has clinical signs or symptoms consistent with acute myocardial infarction or ischemia, followed by omecamtiv mecarbil testing.

Study Outcomes

The primary outcome is a composite of the time to a heart failure event, cardiovascular death, left ventricular assist device (LVAD) implantation, cardiac transplant, or stroke, whichever occurs first. A heart failure event is defined as an urgent clinic visit, emergency department visit or hospitalization for subjectively and objectively worsening heart failure leading to treatment intensification beyond changed oral diuretic therapy.

Secondary outcomes are: all heart failure hospitalizations; the change in KCCQ Total Symptom Score (TSS) from baseline to week 24, week 48, and end of study (scale from 0 to 100; higher score indicates fewer symptoms) in patients with <80 TSS at baseline; the time to all-cause mortality; the time to cardiovascular death; the time to heart failure event; the time to left ventricular assist device (LVAD) implantation/cardiac transplant; and the time to stroke.

Exploratory outcomes are the change in baseline in NT pro-BNP from baseline to week 24 in NT pro-BNP.

Safety

The safety and tolerability profile of omecamtiv mecarbil is evaluated in comparison with a placebo in patients with HFrEF. Participant incidence of reported major adverse cardiac events, including cardiovascular death, cardiac arrest, non-fatal stroke, non-fatal myocardial infarction, and CV hospitalization is reported. Participant incidence of adverse events (AE) is reported.

The primary analysis of the primary composite endpoint uses a likelihood ratio test from a Cox model including baseline estimated glomerular filtration rate (eGFR) and the treatment group and stratified by randomization setting and region. The secondary endpoints, including components of the primary composite endpoint, in addition to total HF hospitalization, and all-cause mortality is assessed using the same Cox model as the primary composite endpoint. Change in NT-pro BNP and KCCQ-TSS from baseline to Week 24 is assessed using a mixed model fit within each randomization setting containing the baseline value, baseline eGFR, region, visit, treatment, and treatment by visit. An omnibus F-test with 2 numerator degrees of freedom is used to test the treatment effect of OM versus placebo.

All deaths, HF events, strokes, and major cardiac ischemic events (myocardial infarction, unstable angina hospitalization, and coronary revascularization) are adjudicated by EHR review by the local site using standardized definitions (Hicks et al, 2015), and 10% are reviewed by a central clinical events committee (CEC).

What is claimed is:

1. A method of treating heart failure in a subject in need thereof, comprising:
    a) administering to the subject a first dose level of a cardiac sarcomere activator (CSA) of about 37.5 mg twice daily for an initial period of time; and
    b) administering to the subject a second dose level of the CSA for a second period of time based on the subject's plasma concentration of the CSA determined after administration of the first dose level of the CSA has started;
    wherein:
    b-i) when the subject's plasma concentration of the CSA is less than 300 ng/mL, the second dose level of the CSA is about 50 mg twice daily;
    b-ii) when the subject's plasma concentration of the CSA is greater than or equal to 300 ng/mL and less than or equal to 750 ng/ml, the second dose level of the CSA is about 37.5 mg twice daily; and
    b-iii) when the subject's plasma concentration of the CSA is greater than 750 ng/ml, the second dose level of the CSA is about 25 mg twice daily; and wherein the CSA is omecamtiv mecarbil, or a pharmaceutically acceptable salt thereof, or a hydrate of any of the foregoing.

2. The method of claim 1, wherein the second dose level of the CSA is about 37.5 mg twice daily.

3. The method of claim 1, wherein the second dose level of the CSA is about 25 mg twice daily.

4. The method of claim 1, wherein the second dose level of the CSA is about 50 mg twice daily.

5. The method of claim 1, wherein the initial period of time is at least about 2 weeks.

6. The method of claim 1, wherein the subject's plasma concentration of the CSA is determined at about 2-4 weeks after the first administration of the first dose level of the CSA.

7. The method of claim 1, wherein the second period of time starts at about 4 weeks after the first administration of the first dose level of the CSA.

8. The method of claim 1, wherein the initial period of time is at least about 2 weeks and wherein the subject's plasma concentration of the CSA is determined at about 2-4 weeks after the first administration of the first dose level of the CSA.

9. The method of claim 1, wherein the initial period of time is at least about 2 weeks; the subject's plasma concentration of the CSA is determined at about 2-4 weeks after the first administration of the first dose level of the CSA; and the second period of time starts at about 4 weeks after the first administration of the first dose level of the CSA.

10. The method of claim 9, wherein the second dose level of the CSA is about 37.5 mg twice daily.

11. The method of claim 9, wherein the second dose level of the CSA is about 25 mg twice daily.

12. The method of claim 9, wherein the second dose level of the CSA is about 50 mg twice daily.

13. The method of claim 1, wherein the CSA is omecamtiv mecarbil dihydrochloride hydrate.

14. The method of claim 1, wherein the subject has chronic heart failure, or a New York Heart Association Class II or III heart failure.

15. The method of claim 1, wherein the subject has a left ventricular ejection fraction of about 40% or lower.

16. The method of claim 1, wherein the subject has a left ventricular ejection fraction of less than 30%.

17. The method of claim 1, wherein the subject has a concentration of NT-proBNP of at least about 1000 pg/mL.

18. The method of claim 1, wherein the CSA is administered orally to the subject.

19. The method of claim 1, wherein the treatment is effective to achieve a target plasma concentration of about 300 ng/mL to about 750 ng/mL during the second period of time.

20. The method of claim 1, wherein the subject's plasma concentration of the CSA is determined only once.

21. The method of claim 20, wherein the treatment is effective to achieve a target plasma concentration of about 300 ng/mL to about 750 ng/mL during the second period of time.

22. A method of treating heart failure in a subject in need thereof, comprising:
  a) administering to the subject a first dose level of a cardiac sarcomere activator (CSA) of about 37.5 mg twice daily for an initial period of time of at least about 2 weeks; and
  b) administering to the subject a second dose level of the CSA for a second period of time based on the subject's plasma concentration of the CSA, wherein the subject's plasma concentration of the CSA is determined at about 2-4 weeks after the first administration of the first dose level of the CSA, and the second dose level of the CSA is administered to the subject at about 4 weeks after the first administration of the first dose level of the CSA;

wherein:
  b-i) when the subject's plasma concentration of the CSA is less than 300 ng/mL, the second dose level of the CSA is about 50 mg twice daily;
  b-ii) when the subject's plasma concentration of the CSA is greater than or equal to 300 ng/mL and less than or equal to 750 ng/ml, the second dose level of the CSA is about 37.5 mg twice daily; and
  b-iii) when the subject's plasma concentration of the CSA is greater than 750 ng/ml, the second dose level of the CSA is about 25 mg twice daily; and wherein the CSA is omecamtiv mecarbil, or a pharmaceutically acceptable salt thereof, or a hydrate of any of the foregoing, and wherein the treatment is effective to achieve a target plasma concentration of about 300 ng/mL to about 750 ng/mL during the second period of time.

23. The method of claim 22, wherein the second dose level of the CSA is about 37.5 mg twice daily.

24. The method of claim 22, wherein the second dose level of the CSA is about 25 mg twice daily.

25. The method of claim 22, wherein the second dose level of the CSA is about 50 mg twice daily.

26. The method of claim 22, wherein the subject has chronic heart failure, or a New York Heart Association Class II or III heart failure.

27. The method of claim 22, wherein the subject has a left ventricular ejection fraction of about 40% or lower.

28. The method of claim 22, wherein the subject has a left ventricular ejection fraction of less than 30%.

29. The method of claim 22, wherein the subject has a concentration of NT-proBNP of at least about 1000 pg/mL.

30. The method of claim 22, wherein the CSA is administered orally to the subject.

* * * * *